(12) United States Patent
Silverstein et al.

(10) Patent No.: US 6,756,368 B1
(45) Date of Patent: Jun. 29, 2004

(54) USE OF COBALT CHELATES FOR TREATING OR PREVENTING VIRUS INFECTION

(75) Inventors: Saul J. Silverstein, Irvington, NY (US); Erik K. Lium, San Mateo, CA (US); Jennifer A. Schwartz, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/612,332

(22) Filed: Jul. 6, 2000

Related U.S. Application Data
(60) Provisional application No. 60/144,346, filed on Jul. 16, 1999.

(51) Int. Cl.[7] .................... A61K 33/24; A61K 31/538; A61P 31/12; A61P 31/16; A61P 31/20
(52) U.S. Cl. ..................................... 514/185; 514/230.2
(58) Field of Search .............................. 514/230.2, 185, 514/184

(56) References Cited

U.S. PATENT DOCUMENTS

| | | | |
|---|---|---|---|
| 5,049,557 A | | 9/1991 | Dori et al. |
| 5,756,491 A | * | 5/1998 | Dori ........................... 514/185 |
| 6,008,190 A | | 12/1999 | Meade et al. |

OTHER PUBLICATIONS

Dunkel et al., (1991) "Ctc 23 Efficacy in Vitro and on Hsv–1–induced Ocular Epithelial and Stromal Disease in the Rabbit" *Antivir. Res. Supp.* 1: 135 (Exhibit 11).
Louie and Meade., (1998) "A Cobalt Complex That Selectively Disrupts the Structure and Function of Zinc Fingers", *Proc. Natl. Acad. Sci. USA*. 95: 6663–6668 (Exhibit 12).

Ostrow et al., (1994) Topical Ctc–96 Accelerates Wart Growth in Rabbits Infected with Cottontail Rabbit Papillomavirus. *Antivir. Res.* 24: 27–35 (Exhibit 13).
Pope et al., (1998) The Anti–herpes Simplex Virus Activity of N–docosanol Includes Inhibition of the Viral Entry Process. *Antivir. Res.* 40: 85–94 (Exhibit 14).
Reusser, P., (1998) Current Concepts and Challenges in the Prevention and Treatment of Viral Infections in Immonocompromised Cancer Patients. *Support Care Cancer*, 6: 39–45 (Exhibit 15).
Vogt et al., (1992) "Antiviral Activity of a Series of Cobalt Containing Complexes Against Herpesvirus Infection in Vitro and in Vivo" *Antivir. Res.* 17: 114 (Exhibit 16).
Wood, M. J., (1996) "Antivirals in the Context of Hiv Disease" *J. Antimicrob. Chemother.* 37: 97–112 (Exhibit 17).

(List continued on next page.)

*Primary Examiner*—Edward J. Webman
(74) *Attorney, Agent, or Firm*—John P. White; Cooper & Dunham LLP

(57) ABSTRACT

A method of treating a subject infected with a virus or a method of preventing viral infection of a subject comprising administering to the subject an effective amount of a compound having the structure:

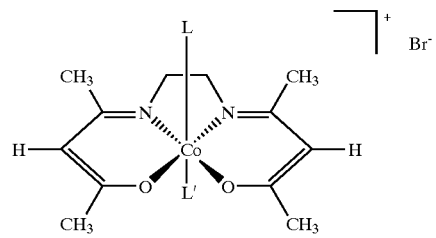

wherein L=L'=2-methylimidazole.

23 Claims, 19 Drawing Sheets

OTHER PUBLICATIONS

Wooley et al., (1992) "The influence of Superoxide Scavenging Compound Ctc 23 on Type Ii Collagen–induce Arthritis in Mice" *Agents Actions* 35: 273–279 (Exhibit 18).

Aguilar, et al. (1999) The Polysulfonated Compound Suramin Blocks Adsorption and Lateral Diffusion of Herpes Simplex Virus Type–1 in Vero Cells. *Virology* 258: 141–151. (Exhibit 4).

Alrabiah and Sacks. (1996) New Antiherpesvirus Agents: Their Targets and Therapeutic Potential. *Drugs*, 52: 17–32 (Exhibit 5).

Asbell et al., (1998) Efficacy of Cobalt Chelates in the Rabbit Eye Model for Epithelial Herpetic Keratitis. *Cornea*, 17: 550–557 (Exhibit 6).

Balfour, H. H, (1999) "Antiviral Drugs" *N. Engl. J. Med.* 340: 1255–1268 (Exhibit 7).

Blum et al., (1998) "Isolation of a Myoglobin Molten Globule by Selective Cobalt (iii)–induced Unfolding", *Proc. Natl. Acad. Sci. USA*. 95: 6659–6662 (Exhibit 8).

Bourne et al., (1997) Evaluation of the Antiviral Activity of an Organometallic Compound in the Guinea Pig Model of Genital Herpes. *Antiviral Research*, 34: A81 (Exhibit 9).

Devin et al., (1993) Efficacy of Ctc Topical Therapy During Hsv–1–induced Epithelial and Stromal Keratitis in the Rabbit. *Invest. Opthal. Vis. Sci.* 34: 1348 (Exhibit 10).

* cited by examiner

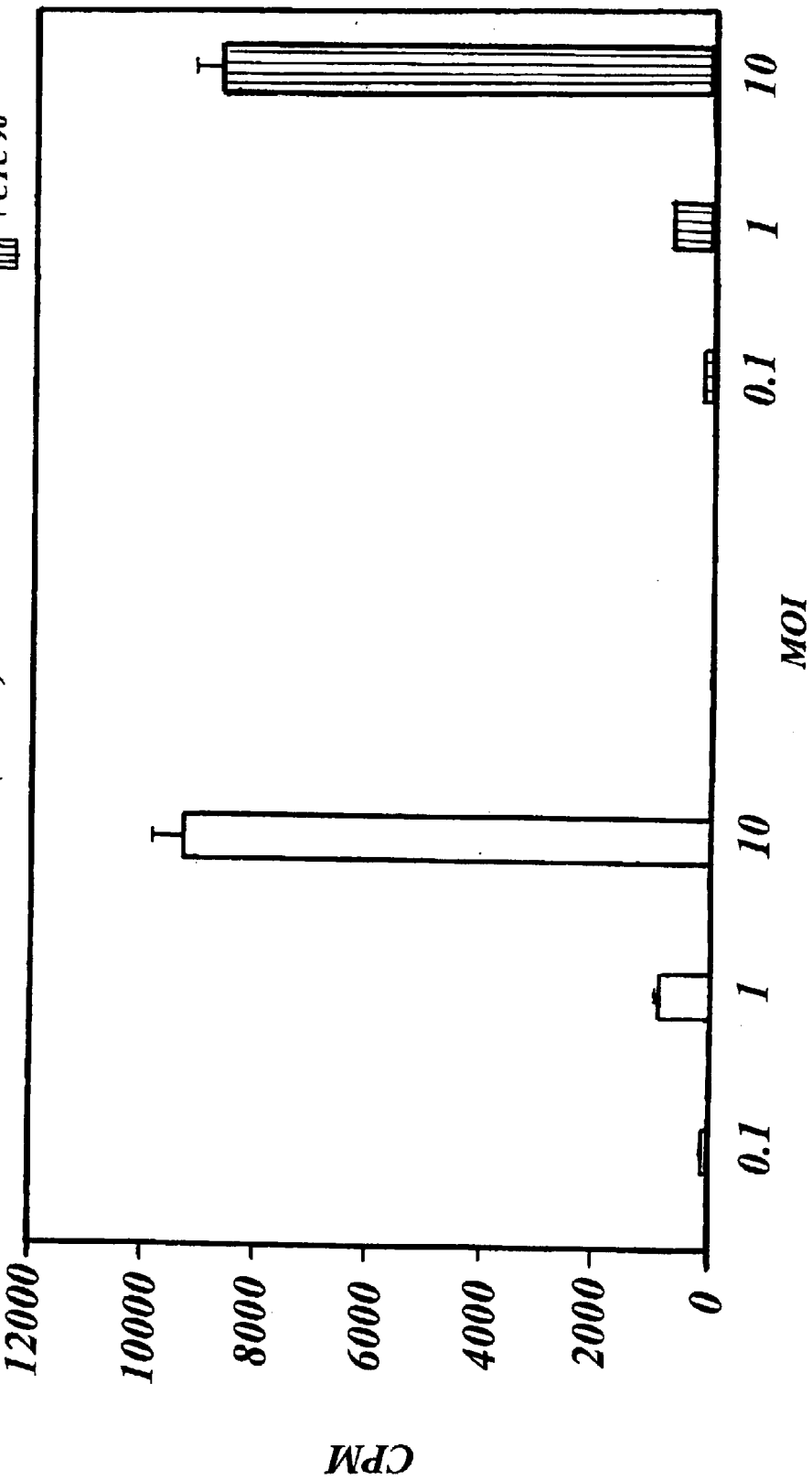

FIGURE 9A
- CTC-96
FIGURE 9B
+ CTC-96
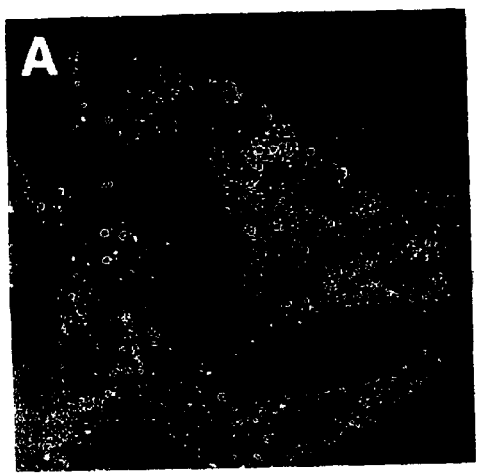
5 min
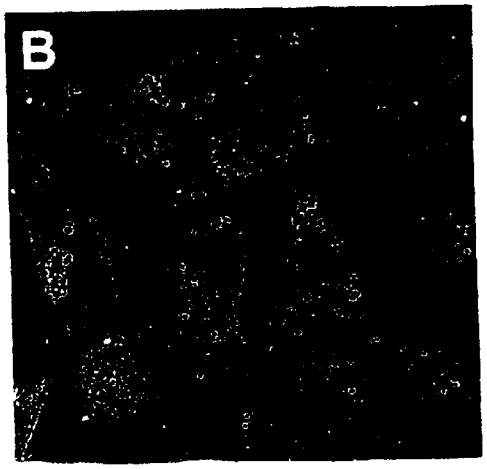
FIGURE 9D
FIGURE 9C
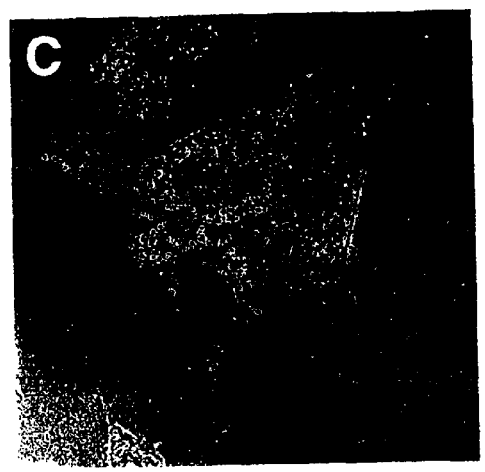
10 min
FIGURE 9E
FIGURE 9F
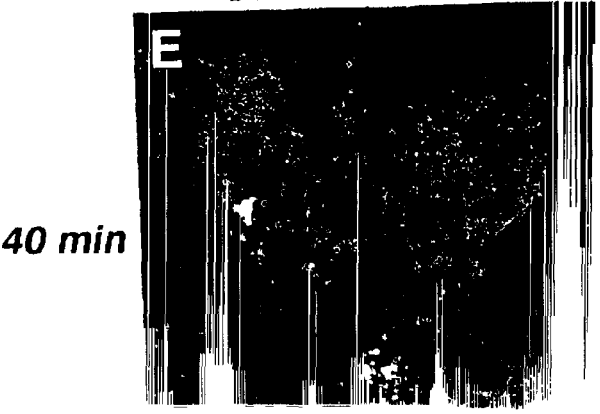
40 min
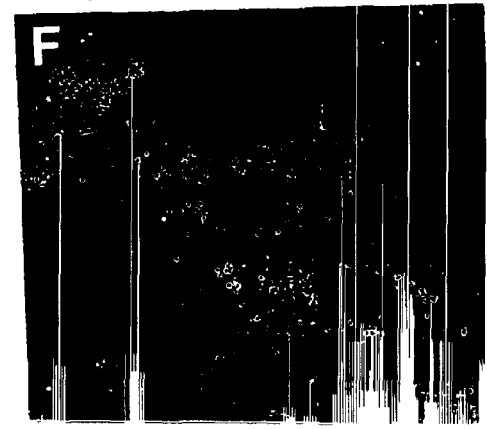

*FIGURE 12*

| Sample | Drug | Relative Counts 1X | 0.1X |
|---|---|---|---|
| 1 | - | 6 | ND |
| 1 | - | 5 | ND |
| 1 | + | 8 | ND |
| 1 | + | 5 | ND |
| M9 | - | 1 | 1 |
| 9 | - | 237 | 40 |
| 9 | - | 289 | 38 |
| 9 | + | 16 | 2 |
| 9 | + | 17 | 2 |

FIGURE 16

| Treatment | Nuc | Cyto |
|---|---|---|
| None/ 5 min | ∙ | — |
| None/ 1 hr | | ⌒ |
| CTC-96/ 1hr | | — |
| Cyclo/ 1 hr | | ⌒ |

USE OF COBALT CHELATES FOR TREATING OR PREVENTING VIRUS INFECTION

This application claims the benefit of U.S. Provisional Application No. 60/144,346, filed Jul. 16, 1999.

This invention has been made with government support under grants from the Public Health Service RR10506 (Shared Instrumentation Grant), CA13696 (Herbert Irving Cancer Center), and AI-33952. Accordingly, the U.S. Government may have certain rights in-the invention.

Throughout this application, various publications are referenced by author, date and citation. The disclosures of these publications in their entireties are hereby incorporated by reference into this application in order to more fully describe the state of the art as known to those skilled therein as of the date of the invention described and claimed herein.

BACKGROUND OF THE INVENTION

Viral infection is the cause of a number of human and animal diseases throughout the world. Considerable effort has been focused on developing treatments for preventing infection and reducing virus pathogenesis.

Infection by the alphaherpesviruses herpes simplex virus type 1 (HSV-1) and type 2 (HSV-2) result in a variety of viral diseases which are distributed worldwide including oral and genital epithelial lesions, encephalitis and ocular keratitis (15, 16, 20, 87, 91). Among these, herpetic ocular infection is the leading infectious cause of blindness in developed countries (45, 52, 53, 87). In immunocompetent and immunocompromised patients herpesvirus infections are among the most frequent causes of virus disease (74, 84, 92). Herpesvirus infections are characterized by their ability to establish latency and reactivate from the latent state (76). Consequently, both primary and recrudescent infections in immunocompromised patients are life-threatening (74, 84, 92).

Several medications exist which are approved for use in the treatment of herpesvirus infections, e.g. aciclovir ("ACV"), penciclovir, valaciclovir, and famciclovir. Derivatives of these are being developed and/or undergoing clinical trials (2, 5, 17). In general these drugs are nucleoside analogs and thus their primary target is virus DNA synthesis (27, 32). A majority of these pharmaceuticals are activated by the HSV protein thymidine kinase ("tk"). Although many of these drugs and their prodrugs target an aspect(s) of the herpes life cycle, they are also proving to be mutagenic or otherwise cytotoxic. In addition, many drug resistant strains are appearing with increasing frequency (13, 14, 17, 29, 30, 51, 66, 77). It is not surprising that these strains have been found to be resistant to the most commonly used of these treatments, ACV. Resistance appears to arise from either altered activation of the drug via aberrant tk expression or substrate specificity (18, 28) or by mutations in other enzymatic processes such as DNA polymerase activity (13, 14, 44, 66, 77). Therefore, new drugs need to be developed which target other aspects of the virus life cycle in order to find treatments which are most effective against the existing drug-resistant strains as well as all the known herpes viruses.

U.S. Pat. No. 5,756,491 relates to antiviral cobalt-organic compounds which are also known as the CTC series of compounds. The disclosures of U.S. Pat. No. 5,756,491, as well as U.S. Pat. No. 5,049,557 referred to therein, in their entireties are hereby incorporated by reference into this application in order to more fully describe the state of the art as known to those skilled therein as of the date of the invention described and claimed herein.

The CTC series of cobalt containing compounds possess anti-inflammatory (93) and anti-viral activity (3, 22, 25, 88). Several CTC complexes have moderate activity in vitro and in vivo against HSV-1 and 2, varicella-zoster virus (VZV), cytomegalovirus and Epstein-Barr virus (3, 22, 25, 88). Previous studies show that CTC-96, structure of which is shown in FIG. 1, a derivative of CTC-23 (3, 22, 25, 88, 93), is the least cytotoxic and most effective of the CTC compounds against HSV-1 and 2 (3, 22). CTC-96 is also effective in inhibiting HSV-1 production in tissue culture (3). In the rabbit eye model, CTC-96 is able to reduce the corneal surface level of HSV-1 and facilitate the recovery from dendritic keratitis (3, 22). It has been suggested that the anti-inflammatory properties of the CTC complexes may aid in recovery from ocular disease (3). Although the anti-herpetic activity of the CTC series has been known for many years, neither the mechanism by which it acts nor the stage of the virus life cycle at which CTC-96 exerts its inhibitory action on HSV-1 has been elucidated.

SUMMARY OF THE INVENTION

The subject invention provides a method of preventing the infection of a cell by a virus comprising contacting the cell with a compound having the structure:

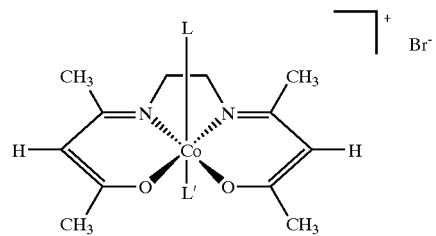

wherein L=L'=2-methylimidazole.

The subject invention also provides a method of treating a cell infected by a virus comprising contacting the cell with a compound having the structure:

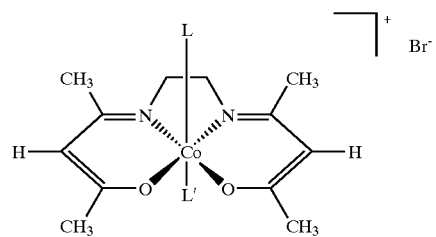

wherein L=L'=2-methylimidazole.

More particularly, the inventive method is useful against either an enveloped viruses or a non-enveloped virus.

In a preferred embodiment, the inventive method is useful against an enveloped virus selected from the group consisting of varicella-zoster virus, vesicular stomatitis virus, and influenza virus.

In another preferred embodiment, the inventive method is useful against a non-enveloped virus selected from the group consisting of poliovirus and adenovirus.

DESCRIPTION OF THE FIGURES

FIG. 3 shows the effect of CTC-96 on HSV-1 attachment. $^3$H labeled HSV-1 was adsorbed to Vero cell monolayers (MOI=100) on ice at 4° C. for 45 min in the presence or absence of 50 μg/ml of CTC-96. The infected cells were washed several times and the amount of free versus bound virus was quantitated (see Materials and Methods). Data are represented as the relative amount of counts per minute (cpm) and are the average of four samples.

FIG. 6 shows HSV-1 DNA replication in the presence of CTC-96. Vero cell monolayers were either mock-infected (M) or infected with HSV-1 in the presence (+) or absence (−) of 50 μg/ml of CTC-96 at a MOI of 5. CTC-96 was added to the infected cells at the indicated hours postinfection (Hpi) Total cell DNAs were harvested at 1 hpi (A), 9 hpi (B) or 24 hpi (C). Ten fold dilutions (1×, 0.1× and 0.01×) of the DNAs were slot blotted onto nylon membranes, hybridized with $\alpha-^{32}P$ labeled probe complementary to the α4 gene and visualized by autoradiography.

FIG. 9 shows the effect of CTC-96 on virus entry visualized by fluorescence dequenching fusion assays. Octadecyl rhodamine B ($R_{18}$) labeled HSV-1 was adsorbed to Vero cells (MOI=100) at 4° C. on ice for 45 min in the presence (B, D, F) or absence (A, C, E) of 50 μg/ml of CTC-96. Infected cells were warmed to 37° C. for 5 min (A, B), 10 min (C, D) and 40 min (E, F). After fixation, the amount of fluorescence dequenching of $R_{18}$ upon fusion of the virion envelope with the plasma membrane was visualized using confocal microscopy. The data are represented as overlays of the fluorescent $R_{18}$ image and the phase contrast image of the same field of cells. Arrows indicate HSV-1 aggregates. (G) The amount of fluorescence dequenching in the presence and absence of 50 μg/ml of CTC-96 was quantitated using flow cytometry. The fusion assay was performed as described above except that after fixation the cells were scraped into PBS and analyzed using a fluorescence activated cell sorter (FACStar). The FACStar was calibrated prior to sample loading using rhodamine calibrate beads.

FIG. 12 shows virus DNA replication in the presence of CTC-96. Vero cells were infected at an moi of in the presence or absence of 50 μg/ml of CTC96. At 1 and 9 hr pi cells were harvested and analyzed for the amount of virus DNA. Each sample was done in duplicate and two concentrations of DNA were applied to the filter for analysis by Southern blot hybridization. The relative intensity of each band was determined using a Molecular Dynamics phosphorimager.

FIG. 16 shows the fractionation of virus DNA. Cells infected with HSV-1 in the absence (None) or presence of either CTC-96 (50 μg/ml) or cycloheximide (100 μg/ml) were harvested at the indicated times post infection and fractionated into nuclear and cytosolic compartments by treatment with detergent. DNAs were extracted from each fraction, transferred to a nitrocellulose membrane using a slot blot apparatus and hybridized to a $^{32}$P-labeled probe to detect virus DNA.

DETAILED DESCRIPTION OF THE INVENTION

Figure 1:
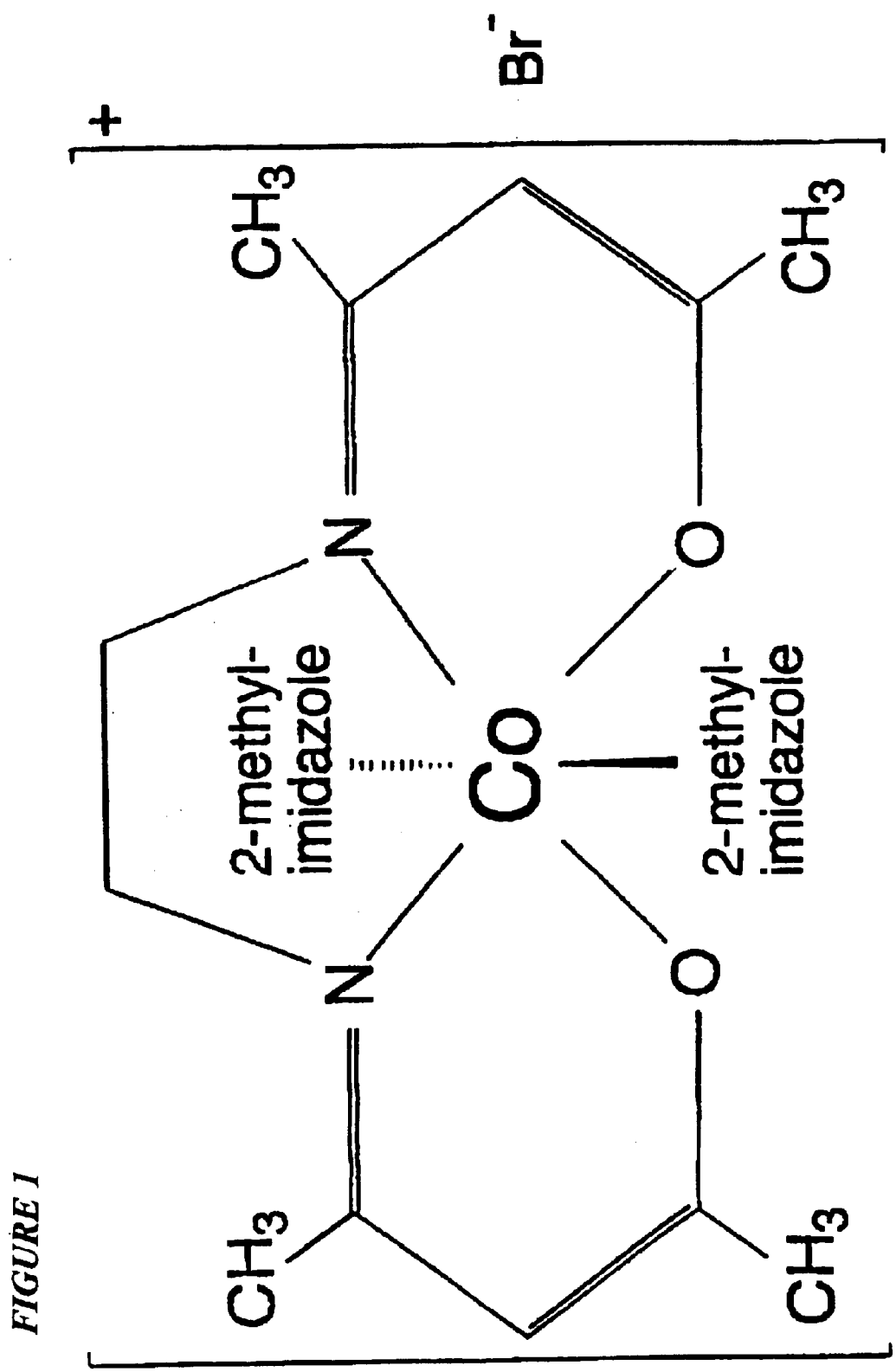
FIG. 1 is a schematic diagram of the chemical structure of CTC-96. 2-MeI denotes 2-methylimidazole.

The subject invention provides a method of treating a subject infected with a virus or a method of preventing viral infection of a subject comprising administering to the subject an anti-viral effective amount of a compound having the structure shown as formula I below:

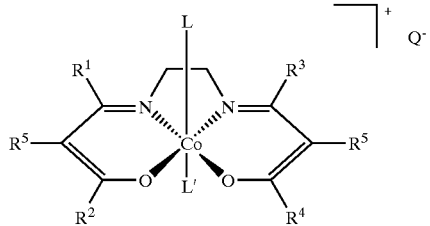

Formula I wherein $R^1$, $R^2$, $R^3$, and $R^4$ may be the same of different and may be an alkyl group, a phenyl group or a substituted derivative of a phenyl group;

wherein $R^5$ may be hydrogen, a halide, an alkoxide group, an alkyl group or OH;

wherein L and L' may be the same or different and may be NH$_3$, an imidazole, a substituted derivative of an imidazole, such as 2-methylimidazole; and wherein Q$^-$ is a soluble, pharmaceutically acceptable negative ion.

The compounds are also described in U.S. Pat. No. 5,756,491, the content of which is incorporated herein by reference.

In a preferred embodiment each of $R^1$, $R^2$, $R^3$, and $R^4$ is CH$_3$; $R^5$ is H or Cl; L=L'=imidazole or 2-methylimidazole; and Q$^-$ is Cl$^-$ or Br$^-$. In the most preferred embodiment the compound has the structure of Formula II below, also refered to herein as "CTC-96":

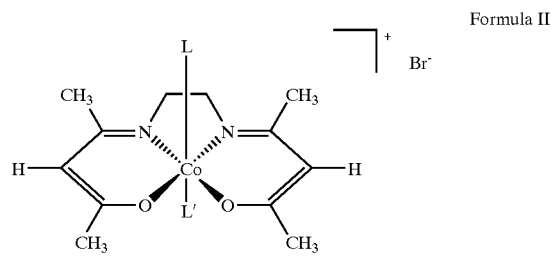

Formula II wherein L=L'=2-methylimidazole.

In another embodiment the invention provides a method for treating a subject infected with an enveloped virus comprising administering to the subject an anti-enveloped virus effective amount of the compound of Formula I.

In yet another embodiment the invention provides a method for preventing infection of a subject by an enveloped virus comprising administering to the subject an anti-enveloped virus effective amount of the compound of Formula I.

The enveloped virus may be but is not limited to HSV-1, varicella-zoster virus, vesicular stomatitis virus, and influenza virus. In the case of influenza, the influenza viruses can be classified into three types, namely A, B and C depending on the serum types of nucleoproteins and membranous proteins.

In a further embodiment the invention provides a method for treating a subject infected with by a non-enveloped virus comprising a anti-nonenveloped virus effective amount of the compound of Formula I.

In yet a further embodiment the invention provides a method for preventing infection of a subject by a non-enveloped virus comprising administering to the subject an anti-nonenveloped virus effective amount of the compound of Formula I.

The non-enveloped virus may be but is not limited to poliovirus and adenovirus.

The anti-enveloped virus effective amount may be an anti-HSV-1 effective amount, an anti-varicella-zoster virus effective amount, an anti-vesicular stomatitis virus effective amount, or an anti-influenza virus effective amount.

The anti-nonenveloped virus effective amount may be an anti-poliovirus effective amount or an anti-adenovirus effective amount.

In a further embodiment, the subject invention provides a method of sterilizing tools and equipment, such as surgical and other medical tools and equipment.

In yet a further embodiment, the subject invention provides a method of sterilizing a room comprising spraying in the room a fine mist comprising the compound of Formula I.

In another embodiment, the subject invention provides a method of sterilizing air comprising dispersing in the air a fine mist comprising the compound of Formula I.

Although compounds described herein can be administered to any subject which is susceptible to viral infection, the compounds are intended for the treatment of mammalian hosts, and especially humans. While the subject may be a human being, any mammal susceptible to the viral infection, such as domestic fowls, pigs, horses and the like may be treated with the compound.

The compound may be formulated into an antiviral pharmaceutical compositions, which comprises one or more of the compounds of formula I above, as the active ingredient in combination with a pharmaceutically acceptable carrier medium or auxiliary agent.

These formulations may be prepared in accordance with the respective conventional methods. The composition may be prepared in various forms for administration, including tablets, caplets, pills, aerosol, an inhelant, a solution, a powder, a capsule or an ointment or can be filled in suitable containers, such as capsules, or, in the case of suspensions, filled into bottles. The compounds of the invention may be administered orally, parenterally, such as by intramuscular injection, intraperitoneal injection, aerosol, intravenous infusion or the like, depending on the severity of the infection being treated.

As used herein, "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-viral compounds of the invention, such as by producing any undesirable biological effect or otherwise interacting in a deleterious manner with any other component(s) of the pharmaceutical composition, its use is contemplated to be within the scope of this invention.

Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known carriers for medicaments may all be suitable as carrier media.

Unit dosage forms for oral administration include, for example, tablets, troches, powders, pills, granules and capsules. For such dosage forms, additives, for example, a binder such as gum arabic, gelatin, sorbitol, tragacanth, polyvinyl pyrrolidone, polyvinyl alcohol, hydroxypropyl methyl cellulose, methyl cellulose, crystalline cellulose or sodium carboxymethyl cellulose, an excipient such as lactose, sugar, saccharose, sucrose, mannitol, corn starch, potassium phosphate, sorbitol or crystalline cellulose, a lubricant such as magnesium stearate, talc, polyethylene glycol or silica, and a disintegrant such as potato starch, low substitution hydroxypropyl cellulose, calcium carboxymethyl cellulose or sodium carboxymethyl starch, may be used alone or in suitable combination. Soft capsules may contain a vehicle commonly employed, such as vegetable oil, polyethylene glycol or glycerol, or an oily suspending agent given hereinafter, a solution, or a wetting agent such as a surfactant.

Liquid formulations may be, for example, an aqueous or oily suspension, solution, syrup or elixir, or a dried product including a freeze-dried substance which can be dissolved in water or in other suitable vehicle at the time of its application. For such liquid formulations, additives, for example, a suspending agent such as methyl cellulose, sodium carboxymethyl cellulose, hydroxypropyl cellulose, hydroxypropylmethyl cellulose, polyvinyl pyrrolidone, polyvinyl alcohol, tragacanth, gelatin or sodium alginate, an emulsifier such as lecithin, sorbitan, a fatty acid ester, gum arabic or tragacanth, a lubricant such as a polyoxyethylene sorbitan fatty acid ester, a polyoxyethylene fatty acid ester, hydrogenated caster oil, sesami oil, soybean oil, propylene glycol, polyethylene glycol or ethyl alcohol, an antiseptic such as methyl p-hydroxybenzoate, propyl p-hydroxybenzoate or sorbic acid, and a sweetener such as a syrup, sucrose, sorbitol or mannitol, may be used alone or in suitable combination.

As the base for a drug for intrarectal administration, an oily base such as cacao butter, witepsol, or triglyceride, or a water-soluble base such as glycerol, glycerogelatin or macrogol, may be employed. As additives for an injection solution, a solublizer such as polyoxyethylene, hardened caster oil or sodiumbenzoate, an isotonic agent such as glucose, sodium chloride or glycerol, and a stabilizer such as sodium sulfite, anhydrous sodium sulfite, sodium metahydrogen sulfite or glycerol, may be used alone or in suitable combination.

For the administration to a respiratory organ such as the nose or bronchus, a formulation such as an aerosol, an inhelant, a solution, a powder, a capsule or an ointment, may be employed. In the case of an aerosol, it may be an oily aerosol formulation comprising a nonionic surfactant such as Alacel or Span 80, an amphoteric surfactant such as lecithin or a dispersant such as oleyl alcohol, a propellant such as butane or Freon.RTM., or an aqeous aerosol formulation comprising an isotonic agent such as physiological saline, a phosphate buffer or an acetate buffer and purified water or distilled water for injection. In the case of a solution, for example, polyethylene glycol, sorbitol, polysorbate or physiological saline may be used as the carrier for the formulation. In the case of a powder, for example, crystalline cellulose, α-cellulose, sodium crosslinked carboxymethyl cellulose, hydroxypropyl cellulose, carboxymethyl starch or amirose may be used as the carrier for the formulation. In the case of an ointment, for example, polyethylene glycol, hydroxyethyl cellulose, methyl cellulose, carboxymethyl cellulose or hydroxypropyl cellulose may be used as the carrier for the formulation.

The antiviral agent of the present invention may take a form which is applied to the mucous membrane of the oral cavity or nose so that the active ingredient is gradually released after the application. As the base to be used for such formulation, a cellulose ether such as methyl cellulose, ethyl cellulose, propyl cellulose, hydroxyethyl cellulose, carboxyethyl cellulose or hydroxypropyl cellulose, as well as polyacrylic acid or carboxyvinyl polymer, may be mentioned.

The antiviral agent of the present invention may also take the form of an antiviral spray.

This invention will be better understood from the Experimental Details which follow. However, one skilled in the art will readily appreciate that the specific methods and results discussed are merely illustrative of the invention as described more fully in the claims which follow thereafter.

Experimental Details

Materials and Methods

Cells and Viruses

Vero cells were maintained in 5% bovine calf serum (BCS; Hyclone Laboratories Inc., Logan, Utah) Dulbecco's minimal essential medium (DMEM; Gibco BRL, Grand Island, N.Y.). Helf, MDCK and A549 cells were maintained in 10% fetal bovine serum (FBS; Hyclone Laboratories Inc., Logan, Utah) DMEM. HeLa cells were maintained in suspension in 7% BCS Joklik's medium (Specialty Media, Lavallette, N.J.) and monolayers in 5% BCS DMEM. All media contained 100 U of penicillin per ml and 100 μg of streptomycin per ml (Gibco BRL).

The wild-type virus strains used were: HSV-1 Glasgow strain 17 (9); poliovirus strain P1 Mahoney (provided by V. Racaniello, Columbia University, N.Y.); adenovirus serotype 2 (Ad2) and Ad-CMV-null (both provided by C. S. H. Young, Columbia University, N.Y.); varicella-zoster virus (VZV) strain Ellen (provided by P. Annuziato and A. Gershon, Columbia University, N.Y.); influenza virus strain PR8 (provided by Mount Sinai School of Medicine, N.Y.);

and vesicular stomatitis virus (VSV) strain Indiana (provided by V. Racaniello, Columbia University, N.Y.).

HSV-1 Preparation (i) Cell-associated HSV-1. Vero cell monolayers were infected at low multiplicities of infection (MOIs) and incubated at 37° C. for 2–3 days. Infected cell were scraped into the media and spun down. The infected cell pellet was washed with phosphate-buffered saline (PBS; 2.7 mM KCl, 1.2 mM KH2PO4, 138 mM NaCl, 8.1 mM Na2HPO4.7H2O), resuspended in 1% BCS DMEM and freeze (−80° C.)-thawed (37° C.) five times. The virus was then titrated on Vero cells. Unless otherwise indicated cell-associated HSV-1(17) was used for infection.

(ii) Partially purified HSV-1. Vero cells were infected at a low MOI and incubated at 37° C. for 2–3 days. Infected cells were scraped into the media, spun at 913×g for 5 min at 4° C., washed with PBS and spun again. The infected cell pellet was resuspended in PBS-ABC (PBS containing 5 mM MgCl2 and 7 mM CaCl2) and incubated on ice for 15 min. The suspension was dounced (15 strokes) in a sterile Wheaton dounce homogenizer using pestle B. The nuclei was spun out at 3,015×g for 5 min at 4° C. The virions in the supernatant were spun down at 20,384×g for 75–90 min at 4° C. and the virus pellet was resuspended in PBS-ABC-ICS-glu (PBS-ABC containing 1% inactivated BCS and 0.1% glucose). The virus was pelleted through a 3 ml sucrose cushion (30% sucrose in 50 mM NaCl, 10 mM Tris pH 7.8) for 2 h at 187,813×g in a Beckman SW41 rotor (6, 26). The virus was resuspended in PBS-ABS-ICS-glu and then titrated on Vero cells.

(iii) 3H labeled HSV-1. Vero cells were infected at a MOI of 1. Ten μCi of [6-3H]-thymidine (19.2 Ci/mmol; NEN Life Sciences Products, Boston, Mass.) per ml of media was added to the infected cells at 2 hours postinfection (hpi) and incubated at 37° C. for 2 days. 3H labeled virions were partially purified from the infected cells as described above.

(iv) Octadecyl rhodamine B (R18) labeled HSV-1. Fluorescence dequenching fusion assays were performed as previously described with slight modifications (38, 39, 70). Partially purified HSV-1 was labeled by addition of 14 nmol of R18 (also known as octadecyl rhodamine B; Molecular Probes Inc., Eugene, Oreg.) in ethanol per 425 μg of virus protein and incubated at room temperature for 1 h in the dark with gentle mixing. Free R18 was removed from R18 labeled virions using a Sephadex G75 column. R18 labeled HSV-1 was eluted off the column with PBS in 1 ml fractions and each fraction was titrated on Vero cells. Labeled virus elutes in the void volume while free R18 remains on the column. It is important to note that concentrations of R18 above 32.9 nmol per μg of virus protein is toxic to HSV-1 (Drs. J. Marcelletti and L. Pope, personal communications).

(v) Syn-virus purification. Vero cells were infected at a low MOI. Syncytia (syn-) containing plaques were isolated and plaque purified 2 more times. Cell-associated syn-virus (vJS17syn-) was prepared as described above.

Plaque Formation in the Presence of Drug.

To determine what concentration of drug was required to reduce plaque formation by herpes simplex virus monolayer cultures of Vero cells were infected with $10^2$, $10^3$ and $10^4$ pfu of virus in the presence of varying concentrations of CTC-96 and the number of surviving plaques was determined. The results of this experiment showed that there was a sharp cutoff in drug sensitivity. At 50 μg/ml plaques formation was reduced by greater than 99% whereas at 25 μg/ml by only 30%. We note that at 50 μg/ml of drug the cell monolayer was severely affected after two days of incubation.

The long term effects of short term exposure to drug were assayed by treating virus suspensions with drug for 1 min. and then diluting the virus-drug solution in medium so that the final concentration of drug is <1 ng/ml. Under this condition we noted that some virus survived treatment (~50%). The result of one of these experiments are presented below in Table 1. It would appear that even transitory exposure to drug results in a marked decrease in plaque formation.

TABLE 1

Effects of Exposure and Dilution on Virus Plaque Formation

| Initial [Drug] μg/ml | Final [Drug] μg/ml | No. of Plaques |
| --- | --- | --- |
| 0 | 0 | 107 |
| 50 | 50 | 0 |
| 100 | 100 | 0 |
| 0.016 | 0.016 | 114 |
| 50 | 0.0083 | 46 |
| 100 | 0.0016 | 23 |

Plaque Assays.

(i) HSV-1. Vero cell monolayers were infected with $10^2$, $10^3$ and $10^4$ plaque forming units (pfu) of HSV-1 in the presence of various concentrations of CTC-96 (REDOX Pharmaceutical Corporation, Greenvale, N.Y.). After 1 h adsorption at 37° C. in 1% BCS DMEM with and without CTC-96, infected cell monolayers were overlaid with methylcellulose overlay media (1.5% methylcellulose, 1% BCS, 100 U of penicillin per ml, and 100 μg of streptomycin per ml in DMEM) containing the indicated amount of CTC-96. Plates were incubated at 37° C. for several days and fixed with methanol. The plates were stained with 0.1% crystal violet and plaques counted.

(ii) Poliovirus. HeLa cell monolayers were infected with dilutions of poliovirus. Dilutions were performed in 0.2% BCS PBS with or without 50 μg/ml CTC-96. Two hundred μl of the diluted virus was added to each monolayer and incubated at 37° C. for 1 h. After adsorption, infected monolayers were overlaid with top agar overlay media (4% top agar, 100 U penicillin per ml, 100 μg of streptomycin per ml, and 5% BCS in DMEM) with or without 50 μg/ml CTC-96. After incubation at 37° C. for 2 days, infected monolayers were fixed with 10% TCA and stained with 0.1% crystal violet.

(iii) VSV. Virus was diluted and adsorbed as described above for poliovirus. After adsorption, infected Vero cell monolayers were overlaid with methylcellulose overlay media and incubated at 37° C. for 2 days. Monolayers were fixed and stained as stated above for HSV-1.

(iv) Influenza virus. Virus was diluted in PBS(+)/BA/PS [PBS containing 0.68 mM CaCl2, 0.49 mM MgCl2, 0.4% bovine albumin (ICN Biomedicals, Inc., Costa Mesa, Calif.), 100 U of penicillin per ml and 100 μg of streptomycin per ml] with and without 50 μg/ml CTC-96. One hundred μl of each dilution was added to MDCK cell monolayers and adsorbed for 30 min at 37° C. Infected monolayers were overlaid with overlay media [0.2% bovine albumin, 2 μg/ml 1:250 trypsin (Gibco BRL), 0.02% DEAE dextran, 1.2% purified agar (Oxoid LTD., Basingstoke, Hampshire, England), 100 U of penicillin per ml and 100 μg of streptomycin per ml in DMEM] with and without 50 μg/ml CTC-96 and incubated at 37° C. for 3 days. Infected cells were fixed and stained as describe above for poliovirus.

Adsorption Assay.

Adsorption of HSV-1 and detection of bound versus free virus was performed as described previously (6). Vero cell monolayers were infected with 3H labeled HSV-1 at a MOI of 100.

Western Blot Analysis.

Vero cell monolayers were infected at a MOI of 5 in the presence or absence of 50 µg/ml CTC-96. Protein preparation and western blot analysis were performed as previously described (54). Briefly, at the indicated times the infected cells were collected by centrifugation, resuspended in 1.5× SDS-PAGE sample buffer, and boiled for 10 min. The proteins were separated by SDS-PAGE and electrophoretically transferred to nitrocellulose membranes. Immunodetection of proteins was performed using the following antibodies: ICP0, rabbit polyclonal antibody CLU7 (54); ICP27, rabbit polyclonal antibody CLU38 (54); glycoprotein B (gB), rabbit polyclonal antibody R69 (provided by T. Kristie, National Institute of Allergy and Infectious Diseases) [Zhang, et al. 1991]; and _TIF, rabbit polyclonal antibody anti-VP16 (Clontech Laboratories Inc., Palo Alto, Calif.). The secondary antibodies used were goat anti-rabbit and goat anti-mouse IgG conjugated to horseradish peroxidase (Kirkegaard and Perry Laboratories, Inc., Gaithersburg, Md.). Immunoblots were developed as previously described (55).

RT-PCR.

Vero cell monolayers were either mock infected or infected. The accumulation of α4 and α27 mRNAs from infected cells was determined as previously described [Lium and Silverstein 1997] by coupled reverse transcription (RT) and polymerase chain reaction (PCR) using the commercial kit, EZ rTth RNA PCR kit (Perkin-Elmer) as specified by the manufacturer with modifications. The primers used during RT were 4-2 and ICP27-L-RT [Lium and Silverstein 1997]. Following RT, secondary primers were added for PCR (4-1 and ICP27-U-RT) (55). These primers result in amplification of a 100 basepair (bp) fragment and a 220 bp fragment from the α4 and α27 genes, respectively.

DNA Replication.

(i) DNA preparation. Vero cells infected with MOI of 5 were infected and maintained in the presence and absence of 50 µg/ml CTC-96. Infected cells were harvested by freezing (−80° C.) at the indicated times postinfection. Total infected cell DNA was extracted as described (54).

(ii) Slot blot analysis. Slot blot analysis was performed as previously described (55). Briefly, equal amounts of nuclear or cytoplasmic infected cell DNAs were blotted onto Gene-Screen Plus using a MINIFOLD II Slot Blot System (Schleicher and Schuell, Keene, N.H.) and cross-linked with a Stratalinker 2400 (Stratagene, La Jolla, Calif.) using UV-irradiation. A 4.5 kB SalI-DdeI fragment from the α4 gene of HSV-1 which had been labeled with [α-32P]dCTP (NEN Life Sciences Products, Boston, Mass.) by random priming (Boehringer Mannheim, Indianapolis, Ind.) was hybridized to the nuclear and cytoplasmic DNAs and washed as specified by the manufacturer. Bands were visualized using autoradiography.

DNA Replication in the Presence of Drug.

A series of experiments were initiated to determine the point in the replication cycle where CTC-96 acts. Our first study examined the effects of drug on replication of virus DNA. Cells were infected at an moi of 5 in the presence of the absence of drug and harvested by trypsinization at 1 and 9 hr post infection. Virus DNA was extracted from cells by selective salt precipitation and the amount of virus-specific DNA was assayed after transfer to a nitrocellulose membrane by Southern blot hybridization using a phophorimager to quantitate signal. The results of a typical analysis are shown in FIG. 12. The results of this analysis suggest that there are equivalent amount of virus DNA associated with infected cells at 1 hr post infection. However, virus DNA replicates vigorously only in the sample that does not contain drug. While there is barely a two-fold increase in the accumulation of virus DNA in drug treated samples the amount of virus DNA in the untreated infected sample increases by about 50-fold. We conclude that there is little if any virus DNA replication in cells infected with HSV in the presence of CTC-96.

Figure 13:
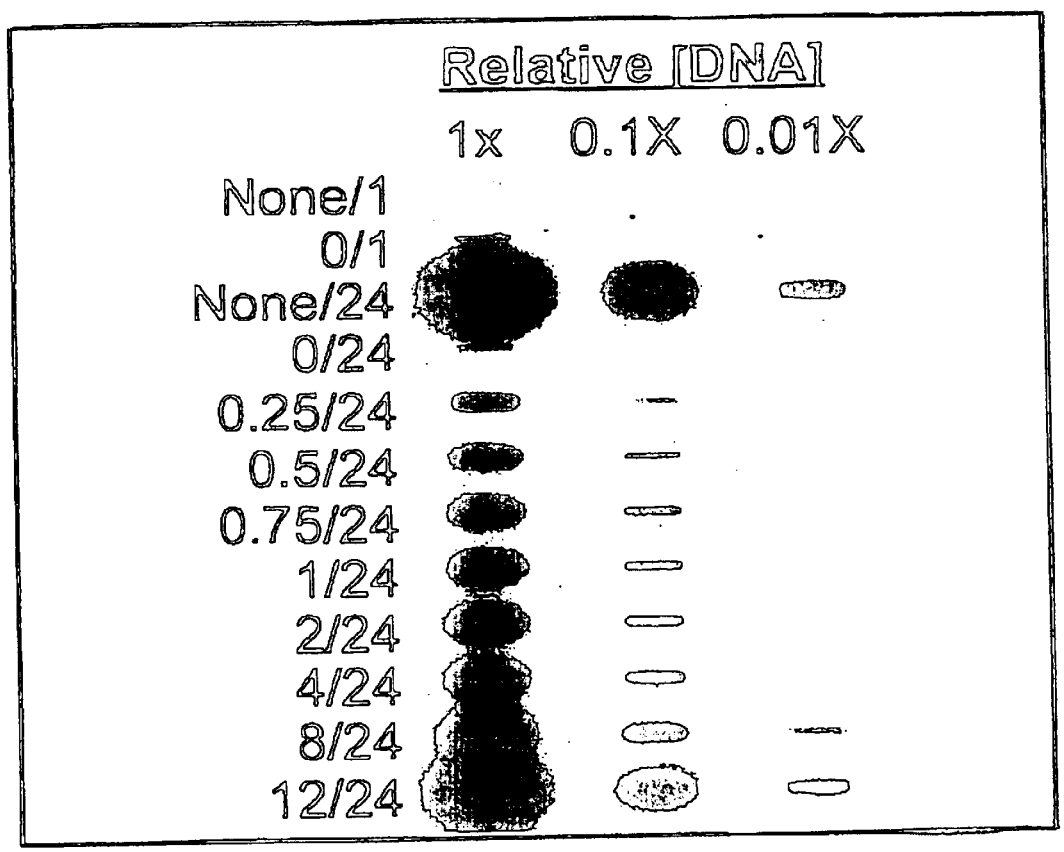
FIG. 13 shows the effect of Temporal Addition of CTC96 on HSV DNA Replication. Vero cell monolayers were infected at an moi of 5 with HSV-1 and treated at the indicated time with 50 μg/ml of CTC-96. At either 1 or 24 hr pi cells were harvested and assayed for the amount of virus DNA that was present in each sample. Three serial 10-fold dilutions of each sample were applied to the filters prior to hybridization with $^{32}P$-labeled probe.

It was conceivable that the drug blocks DNA replication, therefore we asked if addition of CTC-96 at various times post infection had an effect on virus DNA replication. Cells were infected and at various intervals drug was added and left on the infected cell cultures until 24 hr pi. At this time samples were harvested and DNA extracted and analyzed as described above. Analysis of the Southern blot reveals a graded temporal response to the addition of drug such that there is increasingly more virus DNA replication as drug is added at later times post infection. By 12 hr post infection the bulk of DNA replication is complete as there is only a small difference between the hybridization signal generated in an untreated 24 hr sample when compared with a sample treated at 12 hr and analyzed at 24 hr post infection (FIG. 13).

Fractionation of Virus DNA.

Vero cells were infected at a MOI of 10 in the presence and absence of 50 µg/ml CTC-96 or 100 µg/ml cycloheximide. Preparation of nuclear and cytoplasmic fractions were performed as described (69). Briefly, infected monolayers were washed with PBS, 1.75 ml of reticulocyte standard buffer (RSB; 10 mM Tris, pH 7.4, 10 mM NaCl, and 1.5 mM MgCl2) was added to each plate and incubated on ice for 5 min. To each plate, 50 µl of 20% (v/v) Triton X-100 and 200 µl of 10× MAGIK solution [10% (v/v) Tween 40 (Sigma, St. Louis, Mo.) and 5% (w/v) deoxycholate] was added. Cells were scraped off the plates and then homogenized by 4 passes through a 25 gauge needle. The suspension was pelleted at 3,000×g at 4° C. The supernatant was saved as the cytoplasmic fraction to which each of the following was added to the indicated final concentrations: 0.5% (w/v) SDS, 10 mM EDTA, 100 mM NaCl and 200 µg/ml proteinase K. The nuclear pellet was resuspended in RSB containing Triton X-100, MAGIK, SDS, NaCl, EDTA and proteinase K to the final concentrations stated above. The cytoplasmic and nuclear fractions were then incubated at 56° C. overnight, phenol:chloroform extracted and ethanol precipitated. Slot blot analysis was performed as previously described above for DNA replication and by Lium and Silverstein, 1997 (55).

In Situ Hybridization.

Vero cells seeded on two chambered slides were infected with partially purified $^3$H-labeled HSV-1 in the presence and absence of 50 µg/ml CTC-96. At various times post-infection the cells were fixed in methanol:acetic acid (3:1).

Virus Entry Assays.

(i) αTIF immunofluorescence. Vero cell monolayers seeded on cover slips were infected with a MOI of 100 on ice at 4° C. for 45 min. Pre-warmed media (37° C.) was added to each plate, incubated at 37° C. for the indicated times and washed twice with ice cold PBS on ice. The infected cells were fixed in 3.7% formaldehyde in PBS for 30 min at room temperature and washed with PBS. The fixed monolayers were permeabilized in −20° C. acetone at −20° C. for 10 min. Cells were washed with water and then PBS. Fixed cells were incubated in 10% normal goat serum (NGS; Roche, Indianapolis, Ind.) in 0.1% Tween 20 in PBS (PBST) for 20 min at RT and washed twice with PBST. Cover slips were then incubated in PBST containing 1% NGS and 1:200 polyclonal antibody anti-VP16 antibody (Clontech Laboratories, Inc.) for 30 min and washed 6 times with PBST. The infected cell monolayers were then incubated in PBST containing 1% NGS and 1:200 goat anti-rabbit IgG antibody conjugated to fluorescein isothiocyanate (FITC; Kirkegaard and Perry Laboratories, Inc.) for 30 min and washed 6 times with PBST. The cover slips were then mounted on slides in gel/mount solution (Biomeda, Fisher, Springfield, N.J.) and viewed with a 100× lens of a Zeiss LSM 4100 confocal laser scanning system attached to a Zeiss Axiovert 100TV inverted microscope. Each image is the average of 1 µm Z series.

(ii) Fluorescence dequenching fusion assay—Microscopy. The R18 labeled HSV-1 (see above) fusion assay was performed as described above for αTIF immunofluorescence with the exception that after formaldehyde fixation the fixed monolayers were wet mounted on slides in 50 mM DABCO (Sigma) in PBS and viewed using the 100× lens of a Zeiss LSM 4100 confocal laser scanning system attached to a Zeiss Axiovert 100TV inverted microscope. All incubation steps were performed in the dark. Each immunofluorescence image is the average of 1 µm Z series. FIG. 9A shows the immunofluorescence image overlaid on the phase contrast image of the same field of cells.

(iii) Fluorescence dequenching fusion assay—Flow cytometry.

(iv) Electron microscopy. Vero cell monolayers were infected with a MOI of 100 on ice at 4° C. for 45 min with and without 50 µg/ml CTC-96. Pre-warmed media (37° C.) was added and incubated at 37° C. for the indicated times. Plates were washed twice with ice cold PBS on ice, fixed for 1.5 h at room temperature and washed with 0.1 mM cacodylate buffer.

Cell-cell Spread.

(i) Immunofluorescence. Vero cell monolayers were seeded onto cover slips and infected at a MOI of 0.01 in 1% BCS DMEM. At 6 hpi, the media was replaced with 1% BSC DMEM containing 50 µg/ml CTC-96 and 1:200 anti-HSV antibody (in order to neutralize extracellular virus). At 20 hpi the infected monolayers were washed with PBS, fixed, permeabilized and immunodetected as described above for αTIF. The primary antibodies used were rabbit polyclonal CLU38 (anti-ICP27) and (anti-ICP8). The secondary antibodies were goat anti-rabbit and goat anti-mouse conjugated to rhodamine and FITC (Kirkegaard and Perry Laboratories, Inc.), respectively.

(ii) Syncytia formation. Vero cell monolayers were infected with vJS17syn- at a MOI of 0.01. At 6 hpi, the media was replaced with methylcellulose overlay media with and without 50 µg/ml CTC-96. The ability of the virus to form syncytia was then monitored after 2 days at 37° C.

Fluorescence Focus Assay.

A549 or 293 cell monolayers were infected with Ad2 or Ad-CMV-null at 0.1 fluorescence focus units (FFUs) per cell for 2 h in 2% BCS DMEM in the presence and absence of 50 µg/ml CTC-96. At 29 h postinfection the plates were washed twice with PBS and fixed with methanol for 4 min at room temperature. Cells were washed twice with PBS, incubated in 500 µl 1:100 rabbit polyclonal anti-adenovirus serum in PBS for 30 min at room temperature and washed with PBS. Plates were then incubated in 500 µl 1:40 goat anti-rabbit IgG conjugated FITC in PBS. Foci were visualized using a Leitz Dialux microscope with an optical system for the selective visualization of FITC and then counted.

Immunohistochemistry.

HeIf cell monolayers seeded on two chambered slides were infected with 20 µl cell-associated VZV in 1% FBS DMEM in the presence and absence of 50 µg/ml CTC-96. At 28 h postinfection, the slides were washed twice with PBS, fixed in 3.7% formaldehyde in PBS for 30 min at room temperature, and washed again. The infected cells were washed twice with Tris-buffered saline (TBS) and incubated at −20° C. in −20° C. acetone for 10 min. Slides were washed twice with TBS, blocked with 1% goat serum (Sigma, St. Louis, Mo.) in TBS for 20 min at room temperature, and incubated in 200 µl 1:200 rabbit polyclonal anti-ORF 29 in 1% goat serum TBS for 30 min at room temperature. The slides were washed three times with TBS for 5 min each and then incubated with 200 µl 1:200 goat anti-rabbit IgG conjugated horseradish? peroxidase (Kirkegaard and Perry Laboratories Inc.) in 1% goat serum TBS for 30 min at room temperature. Slides were washed three times with TBS for 5 min each. The peroxidase was developed for 5 min using the commercial kit, Alkaline Phosphatase Substrate Kit III (Vector Laboratories Inc., Burlingame, Calif.) according to the manufacturer's directions and then washed several times with water. The slides were viewed with a Leitz Dialux microscope. Endocytosis assay. Vero cells seeded on cover slips were incubated at 37° C. in 5% BCS DMEM with and without 50 µg/ml CTC-96 for various times. The media was them replaced with 5% DMEM containing 1:200 LysoTracker (Molecular Probes, Inc.) with and without 50 µg/ml CTC-96. The cells were incubated at 37° C. for the indicated times, washed on ice with ice cold PBS and fixed at room temperature in 3.7% formaldehyde in PBS for 30 min. The cover slips were washed several times with PBS, mounted in Biomeda gel/mount (Fisher) and viewed with a Leitz Dialux microscope with an optical system for the selective visualization of rhodamine.

Figure 14:
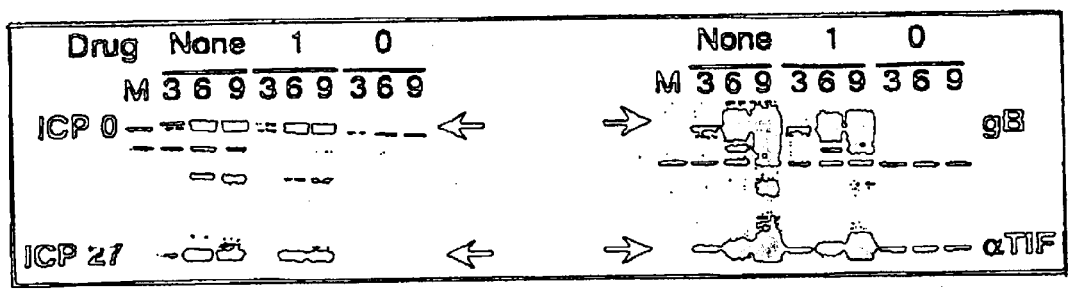
FIG. 14 shows HSV-1 Specified Protein Accumulation in Cells Infected in the present of CTC-96. Vero cells infected at an moi of 5 with HSV-1 in the presence (0 hr pi or 1 hr pi) or absence (none) of drug were harvested at the indicated times post infection and examined by Western blot with antibodies specific for immediate early (ICP's 0 and 27), early gB and late (∝TIF) proteins.

Accumulation of Virus-Specified Proteins in the Presence of Drug. Failure to efficiently replicate virus DNA could result from a specific block of replication per se or because virus-specified gene expression is affected by drug. To address this issue cells were infected with HSV-1 at an moi of 5, 50 µg/ml of drug was either added at time 0, 1 hr pi or not added and at intervals post infection the infected cells were harvested and proteins were extracted and assayed for the presence of virus specified polypeptides by Western blot. Using antibodies that recognize proteins from each of the three kinetic classes we were able to demonstrate that there is little if any synthesis of either ICP0 or ICP27, two immediate early gene products. As a consequence of the failure to detect immediate early protein synthesis there was no measurable accumulation of either gB, an early protein, or α-TIF, a late protein (FIG. 14). In contrast, addition of the drug after one hr of infection has only a small effect on the accumulation of virus-specified proteins from each of the three major kinetic classes (FIG. 14). This finding is what might have been expected from the DNA replication data which demonstrated that replication proceeded in cells where drug was added after the initiation of virus infection. The residual reactivity with α-TIF in the sample treated at T=0 results from protein associated with the infecting virions. There is no increase in the accumulation of this protein during the course of infection. It is not possible to exclude the possibility that virus never enters these cells and that the α-TIF that is detected results from cell associated virus.

Figure 15:
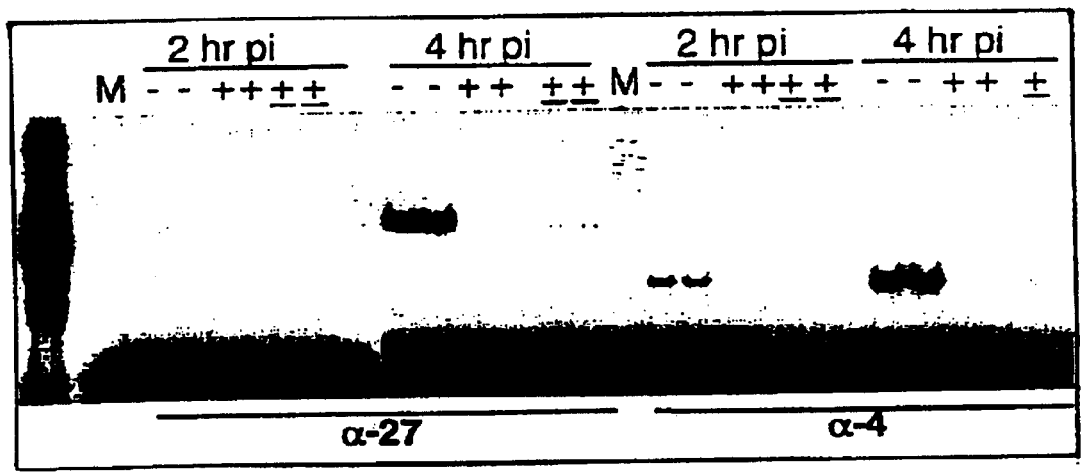
FIG. 15 shows RNA accumulation in cells infected with HSV-1. A stock of HSV-1 was either treated with CTC-96 for 10 and then used to infect Vero cells (+)at an moi of 5, treated and then diluted prior to infection (±) or infected with untreated virus (−). The extreme left lane contains DNA markers and the lanes indicated by an M contain RNA extracted from mock infected cells. At the indicated times pi infected cell RNAs were prepared and examined for the presence of transcripts derived from the ∝27 or ∝4 genes by 20 cycles of RT-PCR using primers specific for transcripts originating from these genes under conditions where amplification was linear. Images were rendered by Phosphorimaging using a Molecular Dynamics StormImager.

The failure to detect virus specified polypeptides of any kinetic class in cells infected in the presence of CTC96 led us to ask if virus transcripts accumulated under these conditions. Accordingly, virus was incubated with 50 μg/ml of drug for 10 min and then either washed out by dilution and used to infect cells or used directly to infect cells. At 2 and 4 hr post infection cells were harvested and total infected cell RNA was prepared for analysis by RT-PCR for the presence of transcripts from the α4 and α27 genes. The results of this analysis reveal that there is no accumulation of these virus-specified RNA's when cells are infected in the presence of drug (FIG. 15). When these studies are carried out to as long as 8 hr pi there is still no detectable accumulation of virus-specified transcripts (data not shown). A small amount of immediate early gene RNA is detected in cells infected with virus exposed to the drug for only 10 min. (FIG. 15). These findings suggest that the virus fails to initiate its transcription program.

Introduction of Virus DNA in the Presence of Drug

To further address the nature of the block to expression of virus genetic information in cells infected with HSV-1 in the presence of CTC-96 we asked if virus DNA entered the nucleus of cells infected in the presence of drug, as a control cells were infected by virus and harvested after 5 min or infected with virus in the presence of cycloheximide which arrests protein synthesis but still permits virus entry and transport of the genome to the nucleus. Following harvest, the nuclei and cytosol were fractionated by detergent treatment and virus DNA was extracted from each compartment for analysis by Southern blot hybridization. The results of this analysis are presented in FIG. 16. After 5 min very little virus DNA is detected in the nucleus or cytoplasm of untreated cells. By 1 hr pi there is abundant virus DNA in the nucleus of cells infected with HSV-1 either in the presence or absence of protein synthesis. In contrast there is still very little detectable virus DNA in either fraction prepared from cells infected in the presence of drug. The residual signal generated from the Nuclear compartment in infected cells harvested at 5 min and in cells infected in the presence of CTC-96 probably results from adventitious sticking of virus particles to cell membranes despite the detergent treatment used to fractionate the cells. This result, in concert with the previous studies, suggests that virus does not enter cells in the presence of drug.

Entry of HSV-1 into Cells Treated with CTC-96.

Figure 17:
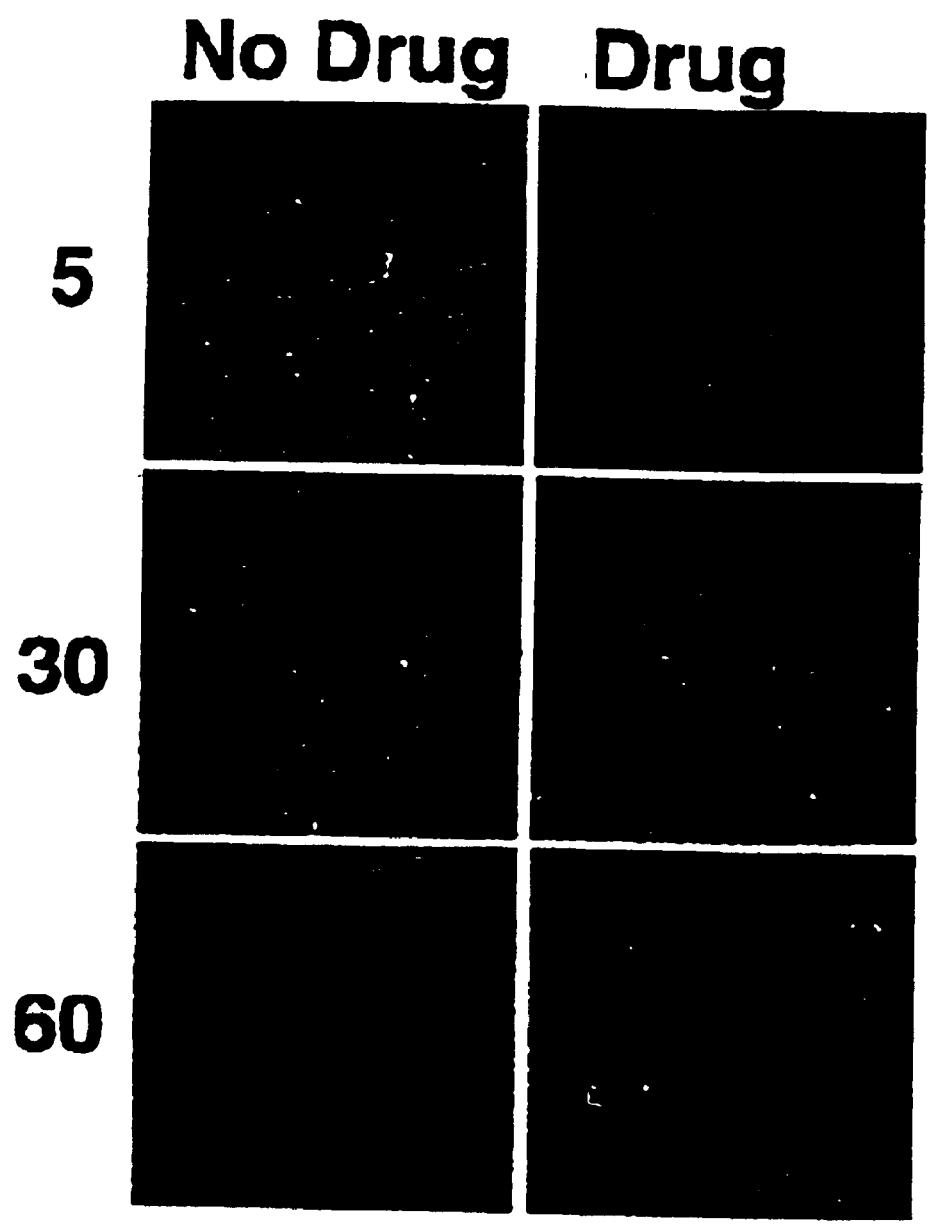
FIG. 17 shows a visualization of virus entry. HSV-1 (moi=100) was allowed to adsorb to cells at 4° C. for 1 hr in the presence or absence of 50 μg/ml of CTC-96. The temperature was then raised to 37° C. and entry was monitored by immunohistochemical analysis using antibody to α-TIF to follow the fate of infecting virus. α-TIF-antibody complexes were visualized by confocal microscopy.

There are several approaches to assessing the ability of virus to adsorb and enter a cell. Perhaps the simplest and most direct is to visualize the transfer of virion-associated proteins from the outside of the cell to its inside. The α-gene transcriptional inducing factor (α-TIF) is a tegument protein that is an integral part of the virion which ultimately ends up in the nucleus shortly after infection to aid in the initiation of transcription of immediate early genes from the genome. It is possible to directly visualize this transfer by immunofluorescence. Accordingly, virus was adsorbed to cells in the presence or absence of drug at 4° C. for 1 hr and then shifted to 37° C. and harvested at 5, 30 and 60 min pi. The samples were fixed and stained with antibody specific for α-TIF. Shown in FIG. 17 are the results of this analysis. It is clear from this study that at 5 min after shift up to 37° C. virus has attached to the periphery of the cells and that there appears to be less virus bound to the drug treated cells. At 30 min post shift the virus has entered the cells and can be found in the cytoplasm and the nucleus of the cell infected in the absence of drug. By contrast there is no evidence for virus entering the cell when drug is present. After 60 the nuclear signal begins to become more disperse and it becomes clear that there is no evidence for α-TIF in cells infected in the presence of drug.

CTC-96 was also tested in accordance with procedures described above for activity against other enveloped viruses (Examples 1–3 below) as well as against non-enveloped viruses (Examples –5 below).

EXAMPLE 1

VZV Infection

Cells
Helf cells were plated at $5 \times 10^5$ cells per chamber on 2 chambred slides in 10% FBS DMEM. When cells were a tightly packed monolayer they were infected.

Infection
Cells were infected with cell associated VZV→20 λ stock in 1% FBS DMEM (2 ml) +/– CTC96. (Vero cells were also infected but in 1% BCS DMEM and incubated @37° C. for ~30 h.)

Figure 18:
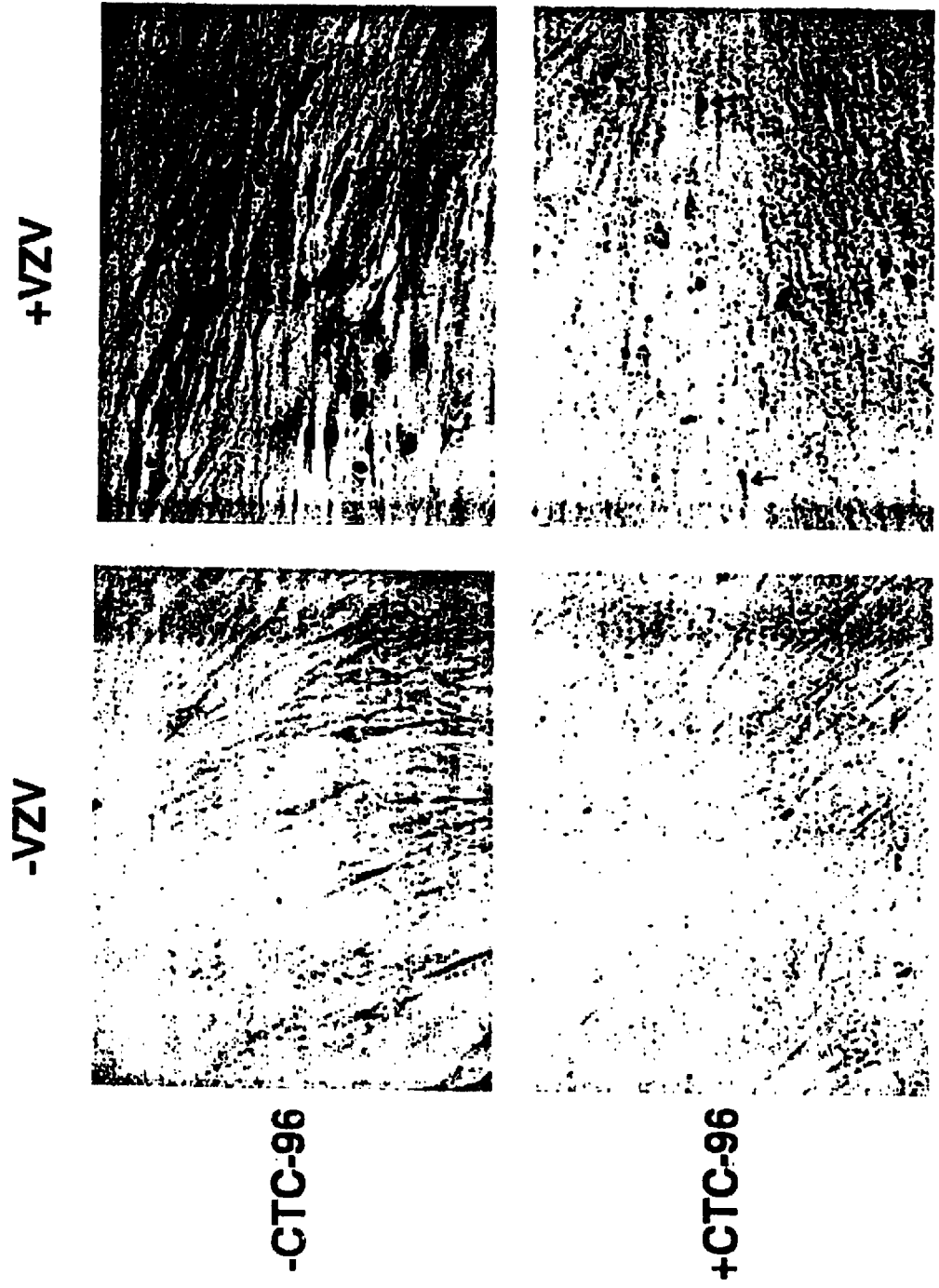
FIG. 18 shows visualization of the effect of CTC-96 on cells infected with VZV. Very few cells were positive for VZV in the presence of CTC-96.

Fixation (Without Removing Chambers)
Slides were washed 2× w/PBS
fixed with 2 ml/chamber of 3.7% for maldehyde in PBS for 30 min @ RT
washed 2× w/PBS
stored @4° C. in PBS Immunohistochemistry
washed 2× w/1× TBS
removed chambers & gaskets
incubated 10 min @–20° C. in –20° C. 100% acetone
washed 2× w/1× TBS
incub. 20 min in 200 λ/chamber area 1% goat serum in TBS poured off block soln.
Incub. 30 min. In 200 λ 1:200 1°AB in 1% goat serum in TBS used either rabbit α or F29 or rabbit α or F14
washed 3×5 min each in TBS
incub. 30 min in 200 λ 1:200 goat αrabbit-phosphatase in 1% goat serum in TBS
washed 3×5 min each in TBS
developed with ABC kit →200 λ soln. For 5 min.
Washed several times w/H₂O
mounted cover slips on slides w/gel/mount →microscope The results are shown in FIG. 18. Very few cells were positive in the presence of CTC-96.

EXAMPLE 2

VSV Infection

Cells
Vero cells were plated @1×10⁶ cells/well on 6 welled plates in 10% BCS DMEM Infection used VSV from V. Racamiello at $6.5 \times 10^8$ pfu/ml

| undil. stock | → -2 (1:100) | → -4 (1:100) | → -5 (1:10) | → -6 (1:10) | → -7 (1:10) |
|---|---|---|---|---|---| diluted in 0.2% BLSPBS +/− 50 μg/ml CTC96
added 100_ of −5, −6, −7 dilutions to cells
incubated @37° C., in—shaking every 5 min
overlaid w/3 ml 3% methyl cellulose in 1% BLSDMEM
incubated @37° C.

Fixation

~24 hpi→nice sited plaques
shook off methylcellulose
fixed ~45 min in MeOH
stained ~45 min in 0.1% crystal violet The cells treated with CTC-96 (50 μg/ml) showed 100% inhibition.

TABLE 2

VSV Infection of cells −CTC-9 and +CTC-96.

|  | −5 | −6 | −7 |
|---|---|---|---|
| −CTC | 553 | 43 | 4 |
| −CTC | 553 | 37 | 5 |
| +CTC | 0 | 0 | 0 |
| +CTC | 0 | 0 | 0 |

EXAMPLE 3

Influenza Infection

Initial trials with influenza virus encountered problems with growing of the cells and infection of the cells. Nonetheless, upon addition of CTC-96 a positive virus inhibitory effect was observed. The magnitude of the effect was not quantifiable.

Subsequent studies show that CTC-96 is effective against influenza virus infection. A study using MDCK cells shows that CTC-96 is effective against influenza virus infection.

EXAMPLE 4A

Adenovirus Infection

Cells 293T cells were plated on 35 mm dishes. Cells should be @$5 \times 10^6$ cells/plate.

Infection

293T Cells were infected with AdCMV-null @ moi=0.1 (i.e. 0.1 FFU/cell)

Virus was absorbed @37° C. for 2 h, rocking every 15 min in 200 λ abs volume virus was diluted in D2 media +/− 50 μg/ml CTC96 D2=2% serum DMEM Plates were overlaid with 2.5 ml D2 +/− 50 μg/ml CTC96 and incub. @37° C. for 28 h (total)

(Media was added drowise to plate because 293T cells are easily popped off plate)

2 plates of cells were incub. In D2 media (no virus) and 2 plates of cells were incub. In D2 media +50 μg/ml CTC96 (to see cytotoxic effect of drug on 293T cells)

Fixation 28 hpi—plates were washed 2× w/25 ml PBS
added 90% MiOH (2.5 ml)—RT 4 min
washed 2× w/2.5 ml PBS—4 min each
stored @4PC in 2.5 ml PBS o.n.
Plates containing 293T cells +or − 50 μg/lm CTC96 were examined
−CTC-96→cells appeared normal (<5% rounded)
+CTC96→at least 50% rounded (CPE)

Staining

Incub. RT, 30 min in 500 λ R∝Ad antiserum (diluted 1:00 in PBS)
washed 2× w/25 ml PBS
Incub. RT 30 min in 500 λ G∝R-FITL (1:40 in PBS)
washed 2× w/25 ml PBS
added 500 λ PBS
stored in dark @4° C.
plates containing 293T cells +or − CTC96 were examined
−CTC96→appeared normal but very dense (<5% rounded)
+CTC96→50% of cells were off of plate the remaining 50% were rounded up (CPE)

TABLE 3

Cells with adenovirus but without CTC-96.

| Plate #1 | | Plate #2 | |
|---|---|---|---|
| Grid | # pos. cells | Grid | # pos. Cells |
| 1 | 27 | 1 | 29 |
| 2 | 17 | 2 | 19 |
| 3 | 30 | 3 | 80 |
| 4 | 20 | 4 | 25 |
| 5 | 21 | 5 | 21 |
| 6 | 17 | | |

Cells with adenovirus and with CTC-96 (50 μg/ml) showed NO FOCI ON EITHER PLATE. Thus, CTC-96 inhibits adenovirus.

EXAMPLE 4B

Adenovirus Infection

Cells

A549s were plated on 35 mm dishes at $8 \times 10^5$ cell/plate in 10% FBS DMEM

Infection

Cells had not reached confluence yet (~80–90%)
Thus, this experiment performed in duplicate.
Ad2 stock→$1.3 \times 10^7$ FFu/ml
for moi=0.1 need $1 \times 10^5$ FFU/plate assuming $1 \times 10^6$ cells need $\times 10^5$ FFU/200 λ
added 19.25 μl stock to 50 μl total of each respective media (+/− 0, 5, 25 or 50 μg/ml CTC96)
Added 200 λ of abs. vol. to each plate
Incubated @37° C. for 2 h, rocking occassionally
One plate→added media alone (no virus, no CTC96)
One plate→added 50 μg/ml CTC96 media only (no virus)
The media used was 2% BCS DMEM
After 2 h-added 3 ml of each respective media
Incubated @37° C. for 28 h (total)

| | Adenovirus | | | | | |
|---|---|---|---|---|---|---|
| | Percent inhibition | | | | | |
| | 0% | | 18% | | 64% | |
| CTC-96 (µg/ml) | 0 | 0 | 25 | 25 | 50 | 50 |
| Plate # | 1 | 2 | 1 | 2 | 1 | 2 |
| Field | 4 | 2 | 3 | 0/2 | 0/3 | 2/0 |
| #1/36 | | | | | | |
| 2/37 | 2 | 1 | 1 | 3/1 | 2/0 | 0/2 |
| 3/38 | 7 | 7 | 0 | 3/0 | 0/1 | 0/1 |
| 4/39 | 4 | 3 | 6 | 4/4 | 1/4 | 2/2 |
| 5/40 | 4 | 6 | 0 | 1/2 | 0/2 | 0/1 |
| 6/41 | 5 | 1 | 3 | 1/5 | 1/0 | 2/0 |
| 7/42 | 5 | 6 | 3 | 3/3 | 1/1 | 1/0 |
| 8/43 | 4 | 5 | 4 | 2/3 | 1/1 | 2/1 |
| 9/44 | 6 | 8 | 6 | 0/2 | 0/1 | 1/2 |
| 10/45 | 4 | 3 | 9 | 1 | 1/0 | 0/3 |
| 11/46 | 2 | 2 | 3 | 4 | 1/3 | 0/0 |
| 12/47 | 3 | 5 | 1 | 0 | 2/4 | 5 |
| 13/48 | 3 | 5 | 1 | 4 | 1 | 2 |
| 14/49 | 4 | 2 | 4 | 3 | 0 | 2 |
| 15/50 | 3 | 3 | 6 | 2 | 1 | 3 |
| 16 | 2 | 6 | 6 | 1 | 2 | 2 |
| 17 | 3 | 7 | 5 | 2 | 2 | 0 |
| 18 | 4 | 4 | 5 | 0 | 2 | 2 |
| 19 | 2 | 6 | 6 | 4 | 2 | 4 |
| 20 | 6 | 3 | 9 | 3 | 1 | 1 |
| 21 | 4 | 4 | 5 | 2 | 2 | 3 |
| 22 | 3 | 3 | 2 | 2 | 0 | 1 |
| 23 | 5 | 6 | 1 | 2 | 3 | 3 |
| 24 | 11 | 6 | 3 | 5 | 2 | 0 |
| 25 | 2 | 4 | 2 | 3 | 2 | 2 |
| 26 | 6 | 108 | 8 | 6 | 2 | 3 |
| 27 | 108 | ↓ | 102 | 3 | 1 | 3 |
| 28 | ↓ | 108/ | ↓ | 2 | 4 | 0 |
| | | 25 = 4.3 | | | | |
| 29 | 108/ | | 102/ | 4 | 1 | 1 |
| | 26 = 4.2 | | 26 = 3.9 | | | |
| 30 | | | | 6 | 2 | 2 |
| 31 | | | | 3 | 5 | 2 |
| 32 | | | | 3 | 4 | 1 |
| 33 | | | | 1 | 1 | 1 |
| 34 | | | | 2 | 3 | 2 |
| 35 | | | | 2 | 0 | 3 |
| | | | | 109 | 73 | 70 |
| | | | | 109/ | 73/ | 70/ |
| | | | | ? = 3.1 | 47 = 1.6 | 46 = 1.5 |

EXAMPLE 5

Poliovirus Infection

Cells

Hela cells (grown from spinner culture) were plated on 6 welled plated @ 1×10⁶ cells/well in 10% BCS DMEM Infection Polovirus strain P1 Mahoney was used to infect cells (essentially titrated virus).

stock was $1 \times 10^9$ pfu/ml serial dilutions in 0.2% BCS PBS +/− 50 µg/ml CTC96 were performed (−1, −2, −3, −4, −5, <u>−6, −7, −8</u>)

Last 3 dilutions were used to infect cells

100 λ abs. Vol. Was used incub. @ 37° C. for 1 h shaking every 10 min overlay media was made:

melted agar 8% top a jar in microwave then equilibrated to 42° C. (should be 45° C.)

Also equilibrated 10% bcs <u>2×dmem</u> TO 42°C.

immediately prior to use DMEM & agar was mixed 1:1

Added 2 ml over lay media to each well (Did not add drug to overlay media)

did not remove abs. vol. from wells

Incub. Plates @37° C. for 2 days

Plaques Assay-Polio once plaques were visible by eye→fixed/stained plates fixed plates by adding TCA to each plate incubated at RT for 10 min removed agar plugs→added crystal violet for 10 min mounted plaques

| | −6 | −7 | −8 | dilutions |
|---|---|---|---|---|
| −CTC96 | 152 | 16 | 0 | → 1.46 × 10⁹ pfu/ml |
| | 140 | 25 | 0 | |

-continued

|        | -6 | -7 | -8 | dilutions |
|--------|----|----|----|-----------|
| +CTC96 | 91 | 10 | 0  |           |
|        | 80 | 9  | 0  |           |

Recovered 58% of −CTC-96.
Therefore, 42% inhibition.
This trial was run in dupilcate and the second run results were obtained as follows:
Poliovirus Plaque Assay
Cells
  Hela cells were plated on 6 welled plates @ 1×10⁶ cells/well on 10% BCS DMEM
Infection
  Infected Hela with Polio P1/Mahoney(In 0.2% BLS PBS) stock (~1×10⁹ pfo/ml)
  1:10→−1→−2→−3→−4→−5→(−6→−7)

```
1:10     → −1 → −2 → −3 → −4 → −5 → (−6 → −7)
         ↘
          ↘1:10 (in 0.2% BCS PBS +50 µg/ml CTC96)
              → −1 → −2 → −3 → −4 → −5 → (−6 → −7)
         ↘      (in 0.2% BCS +100 µg/ml CTC96)
              → → −2 → −3 → −4 → −5 → (−6 → −7)
``` took 100 λ abs. vol. from −6 & −7 dilutions and plated in duplicate (dilutions were not done in duplicate rather the dilutions were infected twice)
Incub. 1 h 37° C., rocking every 10–15 min made overlay media (1:1 8% top a jar 42° C., 2×10% BCS DMEM 42° C.)
added drug (CTC-96) to media immediately prior to mixing with a jar
once made overlay was immediately added to each well (2 ml) containing the respective drug concentration.
Incubate 2 days @37° C.
Fix/Stain
  fixed 10 min RT in TCA: stained 10 min in crystal violet

|         |      | -6 | -7 |          |          | -6 | -7 |               |
|---------|------|----|----|----------|----------|----|----|---------------|
| no drug | TMTC | 45 |    | 50 µg/ml |          | 165| 18 | 42% inhibition|
| no drug | TMTC | 36 |    | 50 µg/ml |          | *  | 16 |               |
|         |      |    |    | 100 µg/ml| cells were dead |    |    |               |
|         |      |    |    | 100 µg/ml| cells were dead |    |    |               |

Results

HSV-1 is inhibited by CTC-96 in tissue culture. The anti-herpetic activity of the CTC complexes against the herpes simplex viruses has been known for many years (3, 22, 25, 88). The majority of these studies have been in vivo protocols which addressed the efficacy of the CTC series of compounds against herpesviruses (3, 22, 25, 88). Comparison of several CTC complexes showed that CTC-96 was the most potent inhibitor of HSV-1 in tissue culture and in the rabbit eye model (3). However, the mechanism(s) by which these drugs inhibit HSV has not been studied.

Figure 2A:
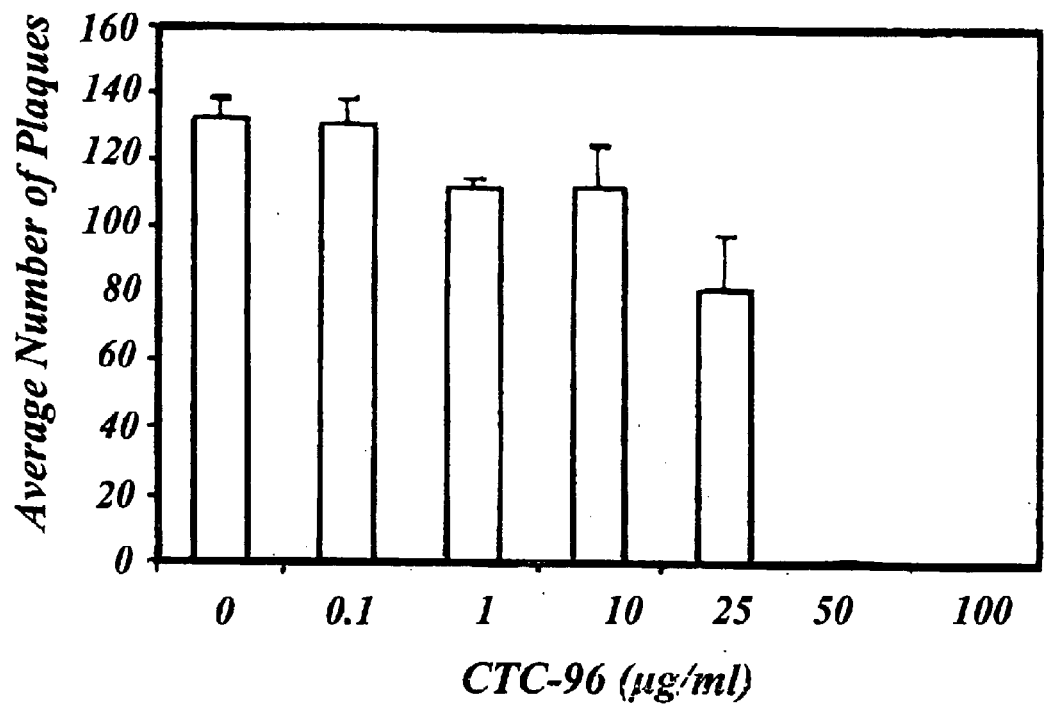
FIGS. 2A and 2B show the effect of exposure to and dilution of CTC-96 on HSV-1 plaque formation in tissue culture. Vero cell monolayers were infected with HSV-1 in the presence of various concentrations of CTC-96. After several days at 37° C., the number of plaques formed were quantitated. Data in 2A represent the average number of plaques formed from four experiments. Data in 2B represent the average number of plaques from two experiments.
Figure 2B:
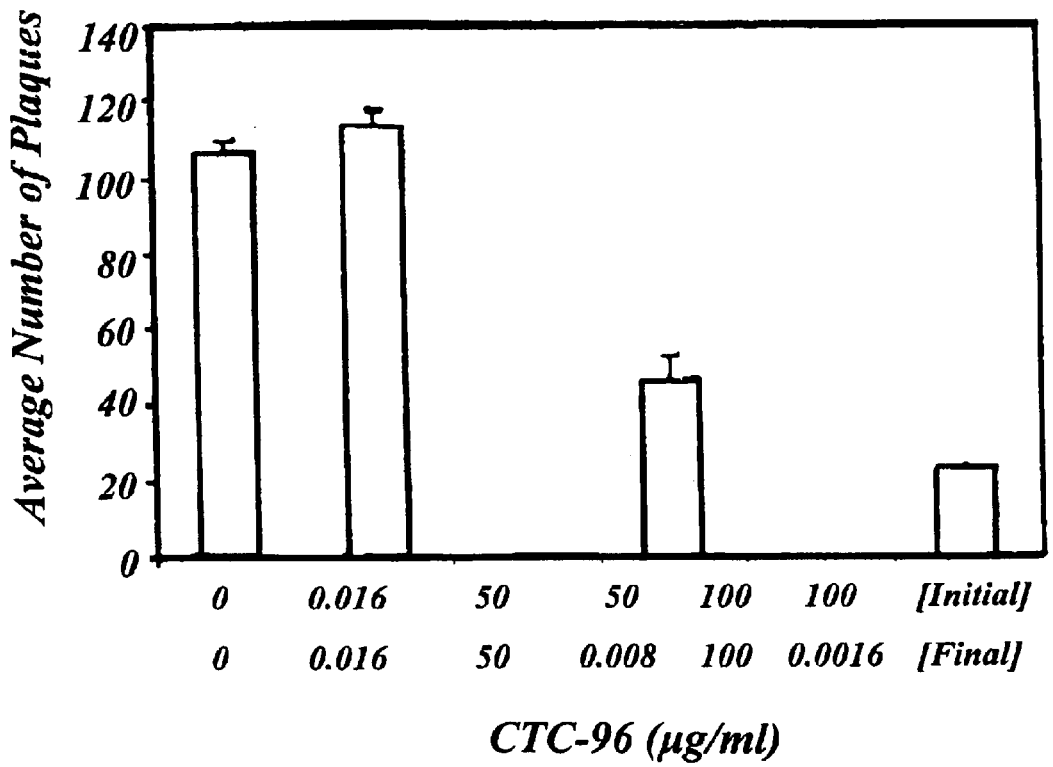

CTC-96 inhibition of HSV-1 in tissue culture (FIG. 2) (3) was non-linear as 25 µg/ml of CTC-96 prevented the formation of approximately 30% of HSV-1 plaques compared to the no drug control (FIG. 2A), while ≧50 µg/ml of CTC-96 completely inhibited plaque formation (FIG. 2). This non-linear inhibitory profile may suggest that 25 µg/ml is not sufficient to saturate its target. Furthermore, CTC-96 must be present throughout infection as dilution of the drug after adsorption of the virus only partially inhibited the formation of plaques (FIG. 2B). However, it was unclear whether this partial blockage was the result of a lag in initiation of infection or whether the drug affected an aspect of the virus or cellular machinery necessary for efficient production of HSV-1 plaques.

In order to address whether CTC-96 directly effects the virions and/or cell monolayer in a irreversible manner virus was incubated with 50 µg/ml of CTC-96 for 30 min on ice or at room temperature. Prior exposure of the virus to the drug had no effect on plaque formation providing CTC-96 was diluted significantly prior to adsorption (data not shown). However, prior incubation of Vero cell monolayers with 50 µg/ml of CTC-96 conferred partial resistance to HSV-1 (data not shown). This resistance decreased as a function of time after drug removal (data not shown). These results suggest that CTC-96 does not irreversibly alter the infectivity of HSV-1 virions, but may perhaps effect a cellular factor(s) involved in supporting HSV-1 production. It is not clear whether the drug is metabolized within the cell, but may be possible as resistance to HSV-1 disappears the longer the cells have not been exposed to drug. However, addition of CTC-96 is only required at the onset of infection which may suggest contrary to the previous hypothesis that CTC-96 is not metabolized. The hypothesis that CTC-96 is acting upon a cellular mechanism(s) is further supported by the observation that prolonged exposure to ³ 50 µg/ml CTC-96 has cytotoxic effects upon Vero cell monolayers (data not shown) (3).

CTC-96 has no effect on attachment of HSV-1 to Vero cell monolayers. CTC-96 inhibits HSV-1 plaque formation. Yet, it is not apparent by what mechanism(s) it achieves this inhibition. A prerequisite for HSV-1 infection is binding of the virion envelope glycoproteins, glycoprotein C (gC) and glycoprotein D (gD), to their cell surface receptors glycosoaminoglycan heparan sulfate (36, 37, 50, 78, 82, 83, 94) and herpes virus entry mediator (HVEM) (63), respectively. Several drugs effective in inhibiting HSV-1 infection have recently been shown to block attachment of HSV virions to their cellular receptors (1). Therefore, the possibility exists that CTC-96 inhibits virion binding to the plasma membrane. We asked whether HSV-1 was able to bind to Vero cells in the presence of 50 µg/ml of CTC-96. HSV-1, grown in the presence of [6-³H]-thymidine, was adsorbed to Vero cell monolayers at 4° C. on ice and the amount of radioactivity that remained cell-associated after several washes was measured. The presence of 50 µg/ml of CTC-96 had no effect on the ability of 3H labeled HSV-1 to bind to Vero cells (FIG. 3). Thus, we reasoned that CTC-96 must inhibit a post-attachment phase of infection.

Figures 4A, 4B:
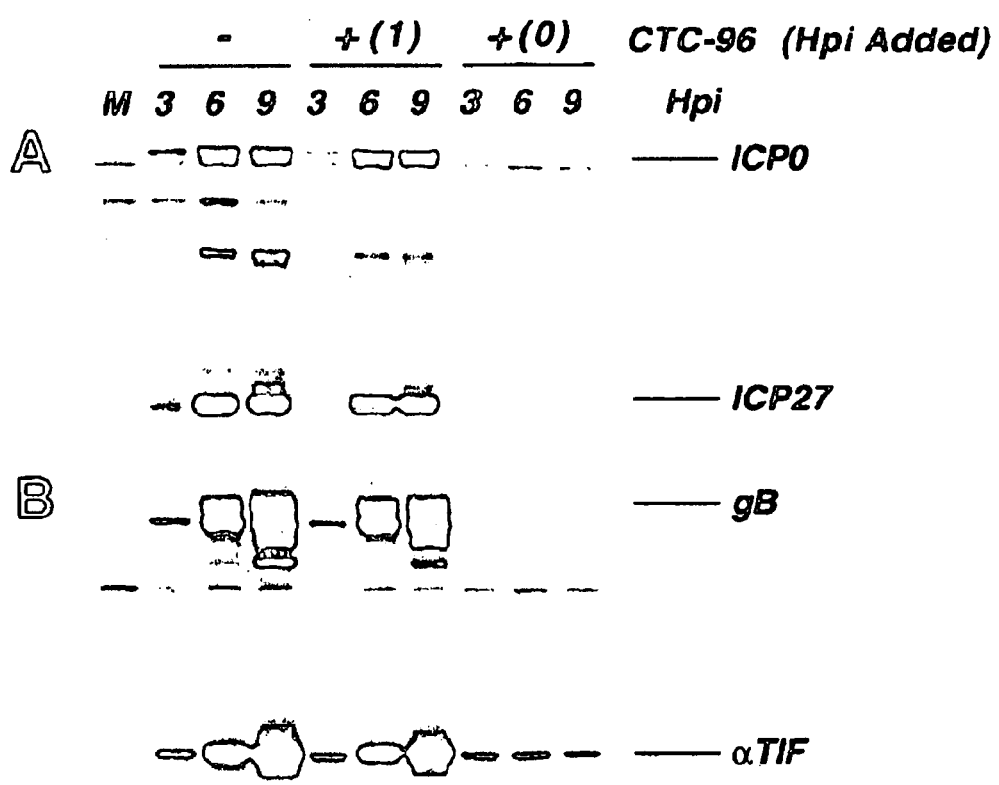
FIG. 4 shows the accumulation of virus specified proteins in the presence of CTC-96. Vero cell monolayers were either mock-infected (M) or infected with HSV-1 at a MOI of 5 in the presence (+) or absence (−) of 50 μg/ml of CTC-96. CTC-96 was added either at the onset of infection (0) or at 1 hour postinfection (1). Infected cell extracts were harvested at the indicated hour postinfection (Hpi). Western blot analysis was performed using either (a) the rabbit polyclonal antibodies CLU7 (anti-ICP0) and CLU38 (anti-ICP27) or (b) the rabbit polyclonal antibodies R69 (anti-gB) and anti-VP16 (anti-αTIF).

Virus proteins do not accumulate when CTC-96 is present during infection. The expression of HSV-1 genes and their gene products occurs in a temporal fashion and are classified into three kinetic classes (α, β, and γ) (41, 42). The production of proteins from all of these classes is required to produce infectious progeny (41, 42). To determine whether the inhibitory action of CTC-96 on plaque formation results in a delay in the temporal order of HSV-1 infection, we examined the accumulation of virus proteins in the presence of 50 µg/ml of CTC-96. CTC-96 prevented the accumulation of gene products from all kinetic classes when present from the initiation of infection (FIG. 3). The appearance of bands reactive to αTIF and gB antibodies when CTC-96 is present from the onset of infection does not result from de novo synthesis of these β/γ proteins (FIG. 3) (35, 40), but rather these bands represent the proteins associated with the infecting virions (FIG. 3B as both αTIF and gB are found within HSV-1 virions (12, 58–60, 96). Yet, when CTC-96 is added subsequent to the initiation of infection, there is little or no effect on the accumulation of the a gene products, ICPO and ICP27 (FIG. 3), nor on the β/γ gene products, αTIF and gB (FIG. 3). Thus, once the cascade of protein synthesis is initiated CTC-96 has no significant effect on virus protein accumulation (FIG. 4). These results suggest that CTC-96 exerts its inhibitory effects on the HSV-1 life cycle after attachment, but at or prior to the synthesis of the a gene products.

A mRNAs do not accumulate unless CTC-96 is present throughout infection. The cascade of HSV-1 gene expression does not require de novo protein synthesis (31, 85, 89) and is initiated by the virion-associated protein, αTIF (11, 71). The first genes turned on by αTIF are the α genes (34, 67). The gene products of two of these genes, α4 and α27, are essential for the subsequent expression of β and γ genes (21, 24, 61, 72, 75). Therefore, we examined whether the α4 and α27 mRNAs were able to accumulate in the presence of CTC-96. In fact, neither the accumulation of α4 nor α27 mRNAs were detectable when CTC-96 was present from the onset of infection (FIG. 4). However, despite a short recovery period α4 and α27 mRNAs began to accumulate if CTC-96 was removed after infection was initiated (FIG. 4) suggesting that the inhibitory effect(s) of CTC-96 are not irreversible. The lack of α mRNA accumulation in the presence of drug suggests that CTC-96 inhibition occurs at or prior to mRNA synthesis.

Temporal prevention of virus DNA replication by CTC-96. In order to further elucidate the stage at which CTC-96 inhibits the HSV-1 life cycle we examined the ability of infected cells to produce virus DNA in the presence and absence of CTC-96. At 1, 9 and 24 hpi, total cell DNAs were prepared, blotted and hybridized with radiolabeled DNA specific for the α4 gene. When CTC-96 was present from the onset of infection and infected cell DNA was harvested at 1 hpi, no detectable difference between the amount of virus specified DNA was observed (FIG. 6A). However, when the infected DNAs were harvested at 9 (FIG. 6B) or 24 (FIG. 6C) hpi there was a dramatic increase in virus DNA replication in the absence of CTC-96 compared to samples infected in the presence of 50 μg/ml of CTC-96 (FIG. 6). Regardless of the harvest time, there is no significant difference in the amount of virus specified DNA in the presence of CTC-96 (FIG. 6).

Figure 5:
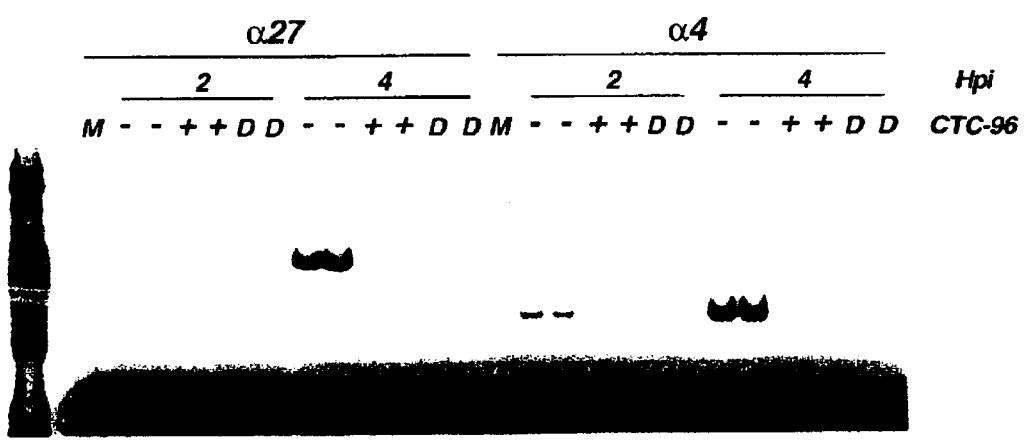
FIG. 5 shows the effect of exposure to and dilution of CTC-96 on the accumulation of αRNAs in HSV-1 infected cells. Vero cell monolayers were either mock-infected (M) or infected with HSV-1 at a MOI of 5 in the presence (+) or absence (−) of 50 μg/ml of CTC-96. Additionally on some samples, CTC-96 was diluted (D). Total cell RNA was prepared at either 2 or 4 hpi. The α4 and α27 mRNAs were amplified by RT-PCR in the presence of $[\gamma-^{32}P]dCTP$ under linear amplification conditions (see Materials and Methods). The amplimers were electrophoretically separated through polyacrylamide gels and visualized by autoradiography. The left hand most lane represents molecular markers. Each condition was performed in duplicate.
Figures 5A, 5B, 5C:
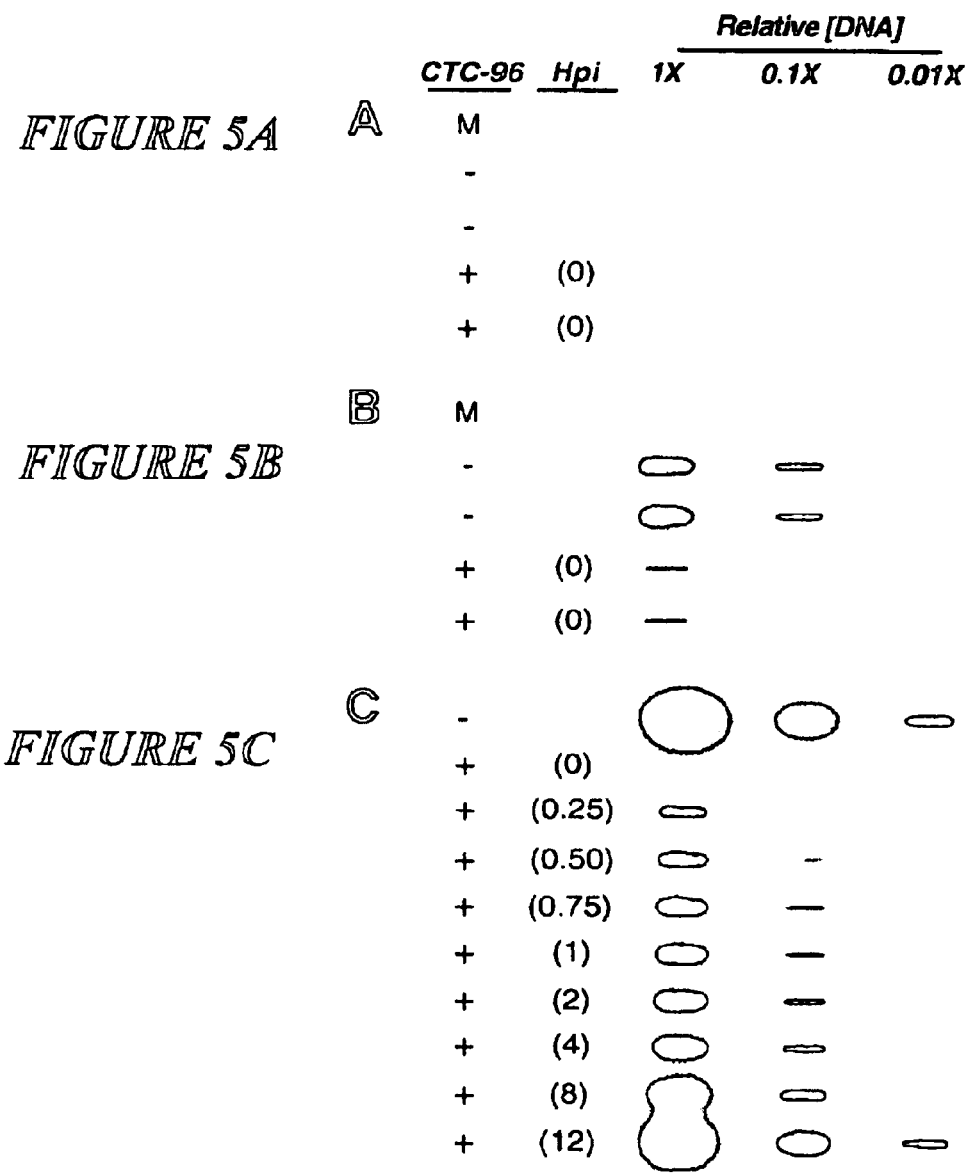

Previously we showed that CTC-96 needed to be present from the initiation of infection in order to completely inhibit virus protein (FIG. 4) and mRNA (FIG. 5) accumulation as well as plaque formation (FIG. 2B). Therefore, we examined whether this observation could be extended to virus DNA replication. When CTC-96 was added to infected cells at later and later times postinfection the amount of virus DNA replication increased (FIG. 6C). However, there was a lag in the amount of virus DNA that accumulated as the amount of DNA present at 24 hpi when CTC-96 was added at 4 hpi (FIG. 6C) appeared equivalent to DNA harvested at 9 hpi in the total absence of CTC-96 (FIG. 6B). These data suggest that like virus protein and mRNA accumulation, virus DNA replication is not inhibited by CTC-96. In addition, there is a temporal requirement for the inhibitory effects of CTC-96.

Virus DNA does not translocate to the nucleus in the presence of CTC-96. In order for virus specified DNA, mRNA and protein synthesis to occur, the virus genome must first be translocated into the nucleus. Since inhibition of the virus processes studied so far required addition of CTC-96 at the onset of infection, we hypothesized that the drug may inhibit nuclear localization of virus genomic DNA. The observed temporal requirement for CTC-96 addition would support such a hypothesis as addition after infection initiation may allow for virus DNA translocation. Furthermore, the observed lag after CTC-96 addition after infection onset may result from inhibition of further virus DNA translocation. To test this hypothesis, we used biochemical and microscopic techniques to examine whether HSV-1 DNA was able to enter the nucleus in the presence of CTC-96. Nuclear and cytoplasmic fractions of infected cell DNA were prepared, blotted and hybridized to a radiolabeled α4 probe. By 5 min postinfection virus DNA was found in the nuclear fraction (FIG. 7A). However, as virus DNA accumulated in the nuclear fraction by 1 hpi in the absence of CTC-96, no significant increase in nuclear associated HSV-1 specific DNA was observed in the presence of CTC-96 (FIG. 7A). Inhibition of HSV-1 DNA translocation was not the result of protein synthesis inhibition as cycloheximide had no effect on the amount of virus DNA associated with the nuclear fraction compared to the no drug control (FIG. 7A).

Figure 8:
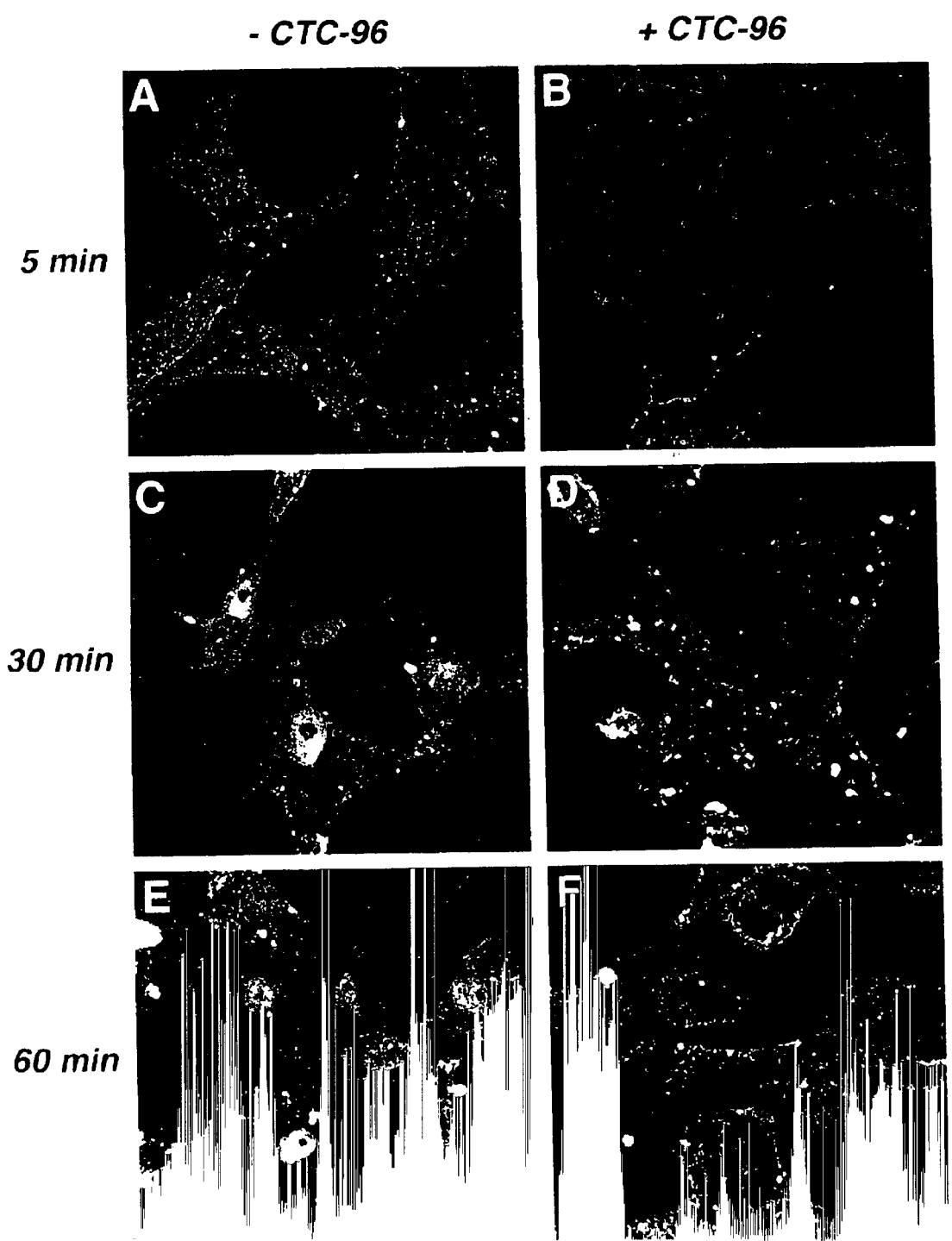
FIG. 8 shows the effect of CTC-96 on virus entry visualized by αTIF immunofluorescence. HSV-1 was adsorbed to Vero cell monolayers in the presence or absence of 50 μg/ml of CTC-96 at a MOI of 100 for 45 min at 4° C. on ice. Infected monolayers were warmed to 37° C. for 5 min (A, B), 30 min (C, D) and 60 min (E, F) after which they were fixed and permeabilized. Immunodetection of αTIF was performed using the rabbit polyclonal antibody, anti-VP16, and the goat anti-rabbit IgG antibody conjugated to FITC as the primary and secondary antibodies, respectively. Immunofluorescence was visualized using confocal microscopy. Each image is the combined average of 1 μm Z-series.

We further confirmed these biochemical data by visually observing the localization of virus DNA. Vero cells were infected with $^3$H-thymidine labeled HSV-1 in the presence and absence of CTC-96. Autoradiographic emulsions, which results in the accumulation of silver grains where radioactivity is present, were used to enhance the $^3$H signal from the HSV-1 DNA. CTC-96 prevented the nuclear accumulation of $^3$H labeled HSV-1 DNA (FIG. 7B) while cells infected in the absence of CTC-96 accumulated virus DNA in the nucleus (FIG. 7B). Furthermore, in the presence of CTC-96 HSV-1 DNA do not display a peri-nuclear localization pattern (FIG. 7B). These results suggest that not only does CTC-96 inhibit nuclear localization of virus DNA, but it also prevents cytoplasmic transport of HSV-1 genomic DNA from the plasma membrane to the nuclear envelope.

αTIF nuclear translocation does not occur when CTC-96 is present. Upon HSV-1 entry/uncoating the capsid containing the virus genome moves through the cytoplasm to the nuclear pores (81). The tegument protein, αTIF, also undergoes translocation to the nucleus (48). In addition, αTIF appears to remain associated with the virus capsid in the cytoplasm (95). Thus, in order to address our hypothesis that CTC-96 inhibits cytoplasmic transport of virus genomic DNA, we determined whether αTIF translocation is also inhibited by CTC-96. Indirect immunofluorescence analysis of αTIF showed that αTIF normally localizes to the nucleus by 30 min postinfection (FIG. 8). This nuclear accumulation is not the result of de novo αTIF synthesis as αTIF protein synthesis did not occur until 2 hpi under these same conditions (data not shown). Yet, when CTC-96 was present αTIF was unable to accumulate in the nucleus by 1 hpi (FIG. 8). Taken together these results suggest the CTC-96 prevents the transport of capsid associated proteins and cargo. Accordingly, CTC-96 must either inhibit virus cytoplasmic transport or HSV-1 entry/uncoating.

CTC-96 inhibits HSV-1 infection in tissue culture by preventing fusion of the virus envelope with the plasma membrane. As we previously showed that CTC-96 did not effect HSV-1 attachment to Vero cell monolayers (FIG. 3), we next examined whether bound virus was able to enter the cell in the presence of CTC-96. In order to accomplish this we utilized a fluorescence dequenching fusion assay developed for influenza virus (57). This assay is performed by labeling the virus envelope with a lipophilic fluorescent dye, octadecyl rhodamine B (also known as $R_{18}$). The central principle of this assay is that under the local concentrations in the virus envelope $R_{18}$ self quenches. However, upon fusion of the virus envelope with the plasma membrane the virus associated $R_{18}$ diffuses laterally in the plasma membrane resulting in fluorescence dequenching. This dequenching can be visually and quantitatively measured by an increase in fluorescence intensity (57). Although, this assay was developed for influenza virus it has successfully extended for use with other enveloped viruses (4, 8, 23, 38, 39, 47, 57, 62, 70, 80). Using confocal microscopy and flow cytometry we examined whether CTC-96 was able to inhibit HSV-1 entry. $R_{18}$ labeled HSV-1 was adsorbed on ice at 4° C. to Vero cell monolayers which allowed virus to bind, but essentially inhibited fusion of the virus envelope with the plasma membrane until the infected monolayers were warmed to 37° C. Addition of CTC-96 prevented HSV-1 fusion to the cell (FIG. 9). By 40 min post-warming there was a dramatic increase in fluorescence in the absence of CTC-96 as seen by confocal imaging (FIG. 9, compare panels A, C and E). However, CTC-96 significantly dampened the amount of fluorescence dequenching (FIG. 9, panels B, D and F). These results were further confirmed by quantitative flow cytometry (FIG. 9G).

Figure 10A:
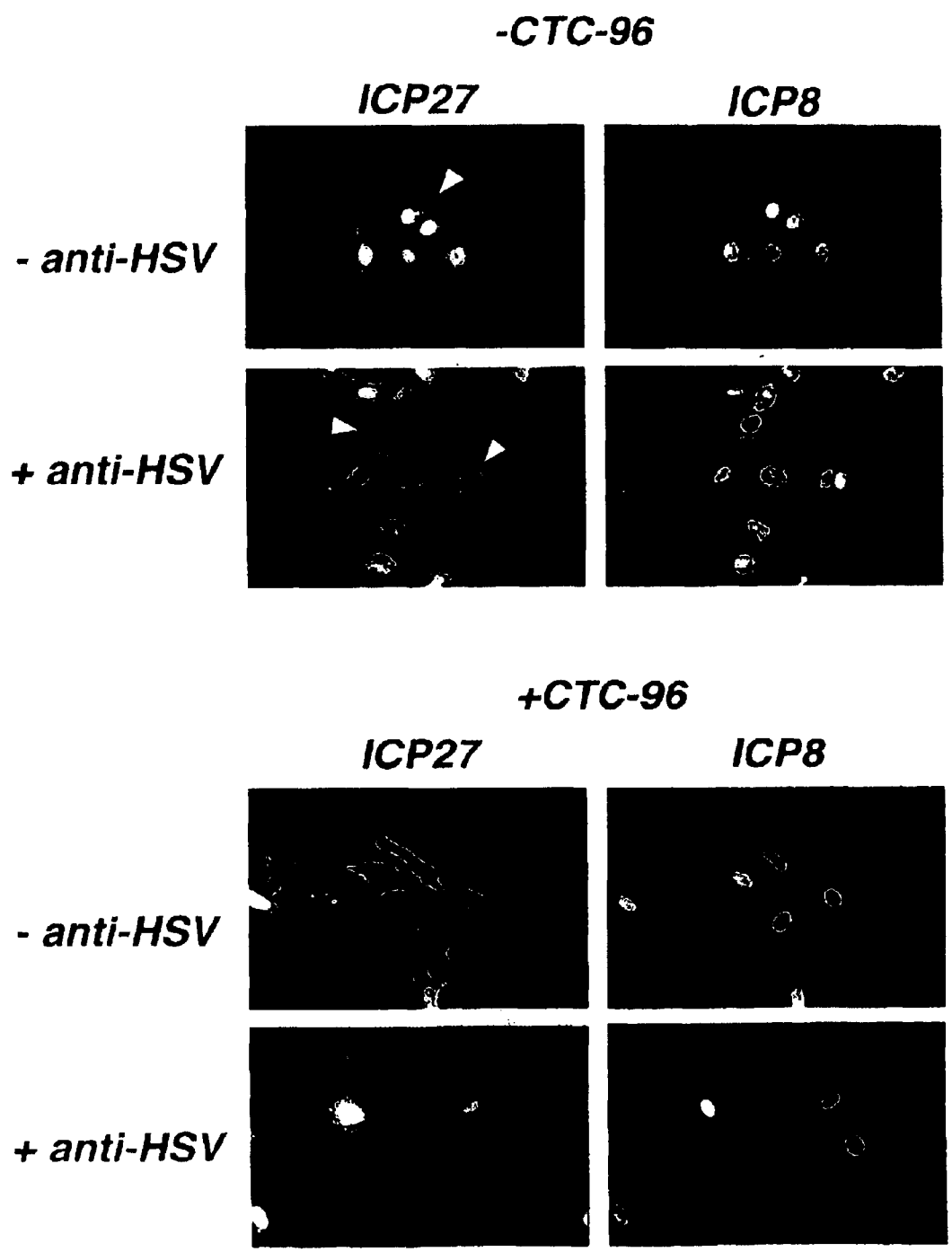
FIG. 10 shows the cell-cell spread of HSV-1 in the presence of CTC-96. (A) (B).
Figure 10B:
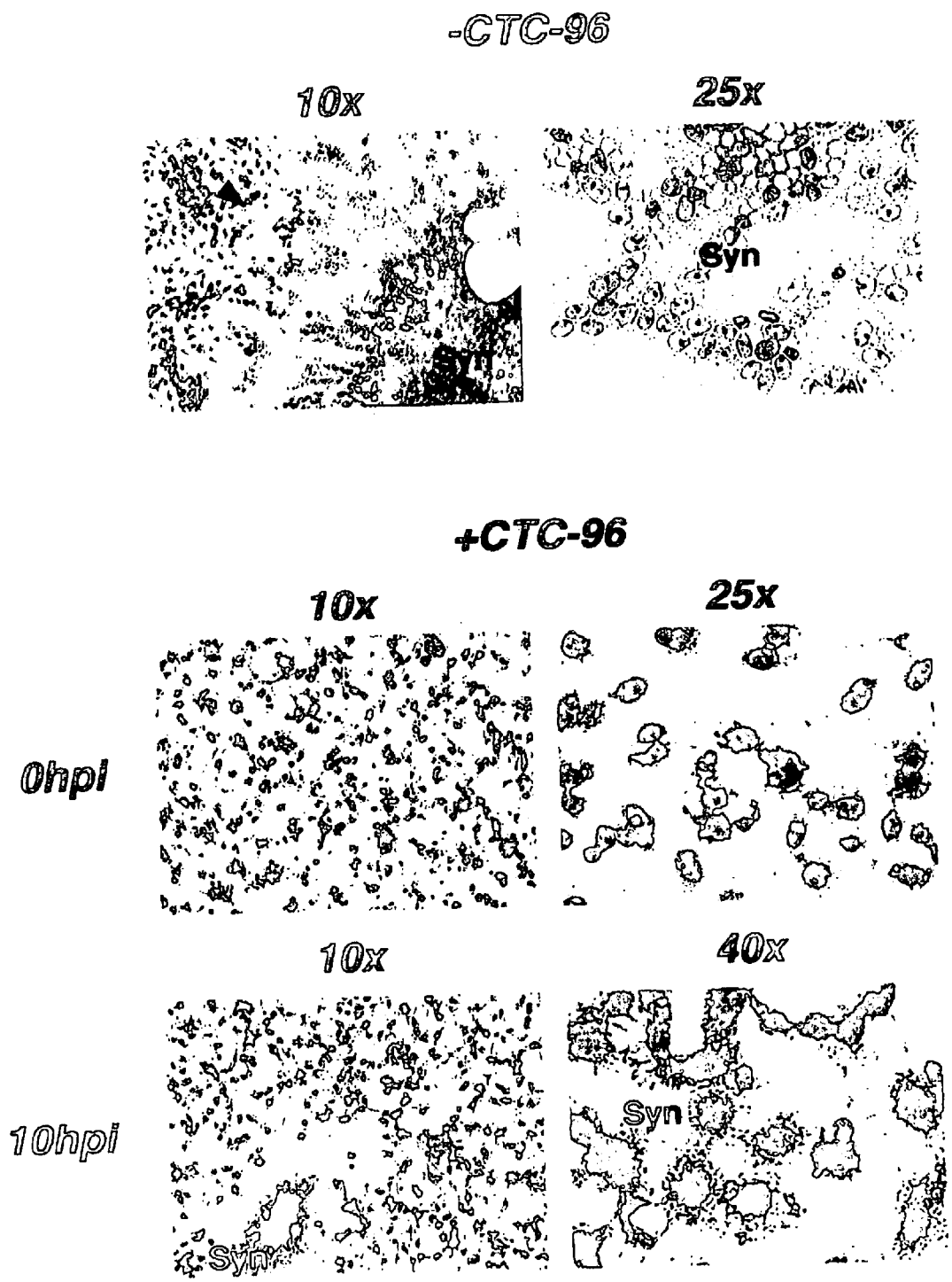
Figure 11A:
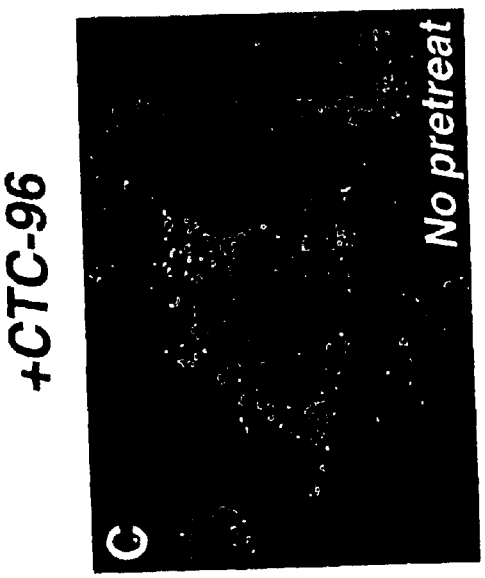
FIG. 11 shows the effect of CTC-96 on endocytosis of a fluid-phase marker.
Figure 11B:
Figure 11C:

Some dequenching was observed in the presence of CTC-96 (FIG. 9). In order to determine if this is an artifact of the assay or if it indicated that HSV-1 was able to fuse to the cell but at a reduced rate, we further examined virus entry using electron microscopic analysis (FIG. 10). Thus, CTC-96 inhibits HSV-1 by preventing virus entry. While CTC-96 appears to ihibit a variety of viruses, it appears to be most effective against enveloped viruses. Table 4 below summarizes the effect of CTC-96 on infection by various viruses.

TABLE 4

Summary of the effect of CTC-96 on infection by various viruses.

| Virus (Strain/Serotype) | Cells | % Inhibition* | Enveloped | Entry via Endocytosis |
|---|---|---|---|---|
| HSV-1 (17)[a][†] | Vero | 100 | Yes | Partial |
| VZV (Ellen)[b] | Helt | 100 | Yes | |
| VSV (Indiana)[a] | Vero | 100 | Yes | |
| Influenza (PR8)[a] | MDCK | ? | Yes | Yes |
| Ad-CMV-null[c] | 293T | 100 | No | Yes |
| | A549 | ND | | |
| Adenovirus (2)[c] | 293T | ND | No | Yes |
| | A549 | 36 | | |
| Poliovirus (P1/Mahoney)[a] | HeLa | 40 | No | |

*Percent inhibition in the presence of 50 µg/ml of CTC-96.
†Summary of FIG. 2.
[a]Data obtained by plaque assay (see Material and Methods).
[b]Data obtained by immunohistochemistry (see Material and Methods).
[c]Data obtained by fluorescence focus assay (see Materials and Methods).
ND: not determined because AD-CMV-null cannot productively infect A549.

Comparison of CTC-96 With Other Drugs.

One attractive target for drugs the initial stage of infection (i.e., entry/uncoating). Several drugs exist which inhibit HSV infection by blocking attachment or fusion of the virus envelope with the plasma membrane. Heparin, a polysulfaonate complex, can block attachment through competitive binding for heparan sulfate proteoglycans. Sumarin, a derivative of urea, is also able to block HSV attachment, but unlike heparin is able to inhibit cell to cell spread of the virus as well. Another drug under study is n-docosanol, a saturated primary alcohol. Unlike heparin and sumarin, n-docosanol does not inhibit binding, but rather fusion of the virus envelope with the cell's plasma membrane. As a result it is also effective against other enveloped viruses which do not require endocytosis for entry. However, one exception to this is influenza A virus. Although it requires the acidic environment of endocytic organelles to accomplish entry it can be inhibited by n-docosanol.

Conclusions

Several complexes in the CTC series of cobalt chelates display in vitro and in vivo activity against the herpes simplex viruses, HSV-1 and 2. The compound CTC-96 exhibits the most potent inhibitory effect against HSV-1 keratitis in rabbits. The experiments described here analyze the toxicity of CTC-96 on HSV-1 infection in Vero cells and determine how CTC-96 inhibits the virus life cycle. There is a sharp cutoff in drug sensitivity where plaque formation is reduced by >99% at 50 µg/mL and only 30% at 25 µg/mL. CTC-96 at 50 µg/mL appears to have no effect on adsorption of virions to Vero cell monolayers. Western blot analysis shows that CTC-96 prevents synthesis of all kinetic classes of virus proteins. RT-PCR also shows that CTC-96 inhibits α4 and α27 gene expression. Furthermore, CTC-96 inhibits DNA replication. Inhibition of nuclear accumulation of virus DNA and virion-associated αTIF in the presence of CTC-96 suggests that CTC-96 prevents nuclear entry of capsid-associated proteins and DNA cargo. Yet, immunofluorescence and in situ hybridization experiments do not reveal peri-nuclear accumulation of αTIF or HSV-1 DNA. We show that CTC-96 inhibits the fusion of the virion envelope with the plasma membrane as determined by microscopy and flow cytometric fusion assays. Taken together these data suggest that CTC-96 inhibits HSV-1 infection at the point of entry and/or uncoating. In addition, the anti-viral effects of CTC-96 are not specific to HSV-1, as it also inhibits varicella-zoster virus, vesicular stomatitis virus, influenza virus, poliovirus and adenovirus infections.

The data shows that CTC-96 is virucidal in nature. It's primary mechanism of action is to prevent virus infection by inhibiting entry. The action of the drug is rapid and irreversible, occurring in less than 10 min. Future studies will focus on the target for inhibition by CTC-96 and identification of the step in entry that is blocked. The approaches for these studies will include isolation of mutants and characterization of the proteins and their domains that interact with the drug.

Discussion

Figure 7:
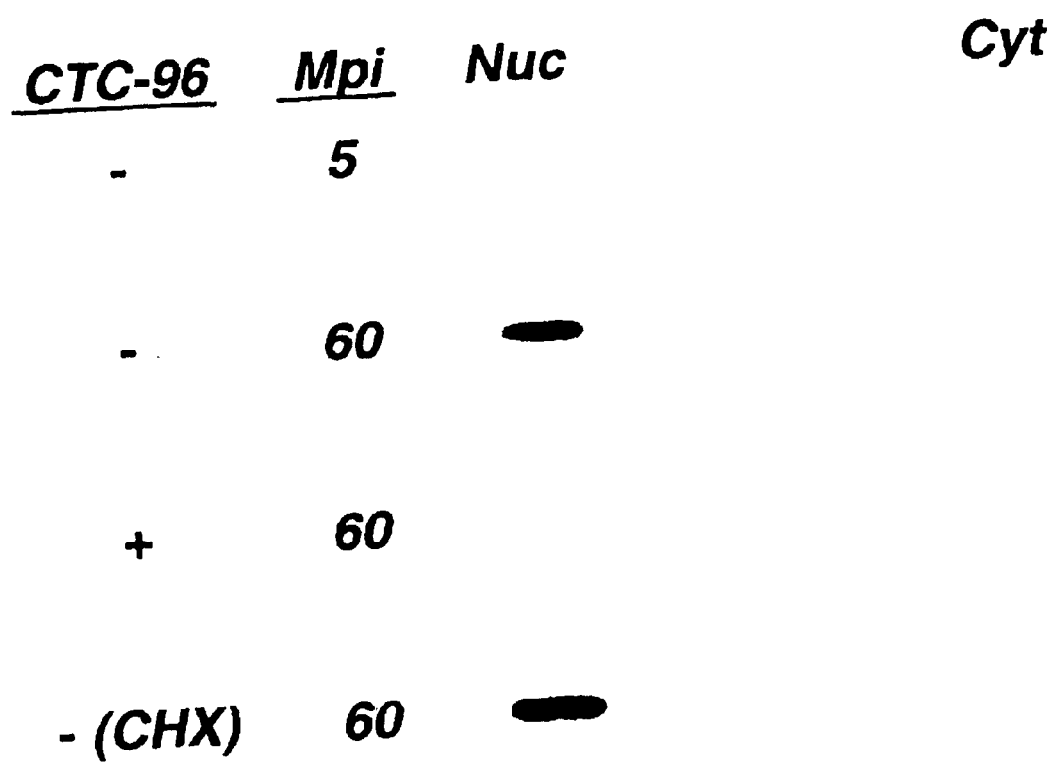
FIG. 7 shows HSV-1 DNA localization in the presence of CTC-96. (A) Vero cell monolayers were infected with HSV-1 at a MOI of 10 in the presence (+) or absence (−) of 50 μg/ml of CTC-96, or 100 μg/ml of cycloheximide (CHX). Infected cells were harvested at either 5 or 60 min postinfection (mpi). Nuclear and cytoplasmic fractions were prepared (see Materials and Methods) and slot blotted onto nylon membranes. Virus DNAs were hybridized with a $\alpha-^{23}P$ labeled probe complementary to the α4 gene and visualized by autoradiography. (B) Vero cell monolayers were either mock-infected (M) of infected with 3H-labeled HSV-1 (INF) in the presence (+) and absence (−) of 50 μg/ml of CTC-96.

The mechanism by which CTC-96 inhibits HSV-1 infection in tissue culture was studied by using a variety of assays that probe the virus processes which are essential for productive infection. Consistent with a previous report (3), we found that concentrations of CTC-96 >50 µg/ml completely inhibited plaque formation (FIG. 2A). Incubation of Vero cells with 50 µg/ml of CTC-96 for several days did however result in cytotoxicity (data not shown). Prior incubation of cell monolayers or HSV-1 with CTC-96 conferred partial resistance (data not shown) and slightly reduced the infectivity of HSV-1 (FIG. 2B), respectively. CTC-96 had no effect on adsorption of HSV-1 to Vero cell monolayers (FIG. 3). However, it did completely inhibit macromolecular synthesis as no virus-specific DNA (FIG. 6), RNA (FIG. 4) or proteins (FIG. 5) were detected in cells infected in the presence of drug. CTC-96 also prevented nuclear accumulation of virion-associated αTIF (FIG. 8) and HSV-1 DNA (FIG. 7). Using a fluorescence dequenching assay, we demonstrated that the fusion of the virus envelope with the cell membrane was inhibited in the presence of CTC-96 (FIG. 9). Therefore, unlike the antiviral drugs currently approved for treatment of HSV-1, CTC-96 prevents entry of virus into cells.

We have now elucidated the point in the virus life cycle at which CTC-96 exerts its inhibitory effects. However, our data do not provide insight into the exact mechanism of inhibition of fusion. CTC-96 may alter the structure of proteins required for membrane fusion by preventing the conformational change of virus glycoproteins and/or cellular receptors which are believed to be important for fusion initiation and completion. Alternatively, CTC-96 may induce a conformation not conducive for membrane fusion. CTC compounds have been shown in vitro to selectively unfold proteins (7). Accordingly, if the cell and virus fusogenic proteins require precise functional conformations, CTC-96 may inhibit their function by preventing protein-protein and/or protein-membrane interactions required for membrane fusion.

Several virus glycoproteins which play a role in the fusion of the virus envelope with the plasma membrane are also involved in cell-to-cell spread and cell fusion. Therefore, to further elucidate the inhibitory mechanism of CTC-96 we examined whether virus was able to spread to adjacent cells. When CTC-96 was added at 8 hpi, HSV-1 infected cells were unable to form multi-celled foci (FIG. 9). Thus, cell-to-cell spread is inhibited whether virus infects adjacent cells by direct contact of the plasma membranes or via the interstitial space. Furthermore, a syncytia forming virus was unable to form syncytia when CTC-96 was added at 1 or 10 hpi (data not shown). Therefore, the inhibition of the fusion processes involved in HSV-1 infection by CTC-96 suggests that there is a general mechanism of fusion shared by these processes.

The CTC compounds were shown to irreversibly bind to and specifically inhibit a DNA binding Zn-finger, Sp1, in vitro (56). Based on this observation it was postulated that the antiviral activity of the CTC compounds could inhibit HIV-1 by binding to Zn-finger containing nucleocapsid proteins as well as to Sp1 which may be important for HIV-1 virus transcription (56). Furthermore, the cytotoxic effects of CTC-96 may result from in vivo inhibition of cellular and viral Zn-finger containing proteins. The HSV-1 immediate-early gene promoters contain numerous Sp1 sites (46) which might provide secondary targets for CTC-96 if it enters cells. However, these hypotheses seem unlikely in light of our results. It is plausible that CTC-96 does not efficiently enter cells considering the temporal requirement for addition of CTC-96 on virus inhibition. This is further supported by our observation that there is only a negligible drop in virus titers when CTC-96 is added at 16 hpi and virus is harvested 4 hours later (data not shown). Hence, CTC-96 does not appear to act intracellularly. Therefore, based on our observations of the inhibitory effects of CTC-96 on fusion, CTC-96 may be harmful to cells in tissue culture by preventing global and/or local membrane dynamics, a vital cellular process. Despite its toxic effect on cells in culture, 50 µg/ml of CTC-96 does not appear to be toxic in animal models (3, 22, 25, 88).

We have as of yet been unable to isolate CTC-96 resistant viruses. This suggests that either CTC-96 targets one or more essential cellular or virus components or it effects a global process such as membrane dynamics. If membrane fluidity is altered by CTC-96 it would need to be reversible as the partial resistance conferred by preincubation with CTC-96 disappears upon dilution of the drug. Thus, inhibition by CTC-96 on virus entry and its effect on cell viability has implications for a global inhibitory mechanism on the coalescence of membranes.

The appearance of ACV-resistant herpesviruses in patients significantly intensified the effort to develop drugs which inhibit an aspect of the virus life cycle different from the current nucleoside analogs used in treatment against the herpesviruses. One attractive target for anti-herpetic drugs is the initial stage of infection (i.e., entry/uncoating). Several drugs exist which inhibit HSV infection by blocking attachment or fusion of the virus envelope with the plasma membrane. Heparin, a polysulfonate complex, can block attachment through competitive binding for heparan sulfate proteoglycans (1). Sumarin, a derivative of urea, is also able to block HSV attachment, but unlike heparin it is also able to inhibit cell-to-cell spread (1). Another drug currently being studied is n-docosanol, a saturated primary alcohol. Unlike heparin and sumarin, n-docosanol does not inhibit virus binding, but rather fusion of the virus envelope with the cell's plasma membrane (70). As a result, it has a broad spectrum and is also effective against other enveloped viruses including influenza A virus (70).

In view of a previous report that CTC-96 inhibits infection by other enveloped herpesviruses (88), it is likely that a similar inhibitory mechanism(s) acts upon these viruses. Consistent with previous reports (88), we observed inhibition of VZV plaque formation by CTC-96 (data not shown). It would be interesting to determine if CTC-96 is also able to inhibit enveloped viruses outside the herpesvirus family. Despite differences in the fusogenic apparatus at the atomic level, it has been proposed that several enveloped viruses share an analogous process in membrane fusion (33, 43, 49, 90). Analysis of the efficacy of CTC-96 against other viruses could reveal a common mechanism(s) of membrane fusion between viruses and cells. CTC-96 may provide a new avenue for inhibiting highly mutagenic viral agents as membrane fusion is an essential infectious process for enveloped viruses.

References

1. Aguilar, J. S., M. Rice, and E. K. Wagner. 1999. The polysulfonated compound suramin blocks adsorption and lateral diffusion of herpes simplex virus type-1 in Vero cells. Virology. 258:141–151.
2. Alrabiah, F. A., and S. L. Sacks. 1996. New antiherpesvirus agents: their targets and therapeutic potential. Drugs. 52:17–32.
3. Asbell, P. A., S. P. Epstein, J. A. Wallace, D. Epstein, C. C. Stewart, and R. M. Burger. 1998. Efficacy of cobalt chelates in the rabbit eye model for epithelial herpetic keratitis. Cornea. 17:550–557.
4. Bagai, S., and R. A. Lamb. 1995. Quantitative measurement of paramyxovirus fusion: differences in requirements of glycoproteins between simian virus 5 and human parainfluenza virus 5 of Newcatle disease virus. J. Virol. 69:6712–6719.
5. Balfour, H. H. 1999. Antiviral drugs. N. Engl. J. Med. 340:1255–1268.
6. Banfield, B. W., Y. Leduc, L. Esford, K. Schubert, and F. Tufaro. 1995. Sequential isolation of proteoglycan synthesis mutants by using herpes simplex virus as a selective agent: evidence for a proteoglycan-independent virus entry pathway. J. Virol. 69:3290–3298.
7. Blum, O., A. Haiek, D. Cwikel, Z. Dori, T. Meade, and G. H. B. Gray. 1998. Isolation of a myoglobin molten globule by selective cobalt(III)-induced unfolding. Proc. Natl. Acad. Sci. USA. 95:6659–6662.
8. Blumenthal, R., A. Bali-Puri, A. Walter, D. Covell, and O. Eidelman. 1987. pH-dependent fusion of vesicular stomatitis virus with Vero cells. J. Biol. Chem. 262:13614–13619.
9. Brown, S., D. A. Ritchie, and J. H. Subak-Sharpe. 1973. Genetic studies with herpes simplex virus type 1. The isolation of temperature-sensitive mutants, their arrangement into complementation groups and recombination analysis leading to a linkage map. J. Gen. Virol. 18:329–346.
10. Cai, W., B. Gu, and S. Person. 1988. Role of glycoprotein B of herpes simplex virus type 1 in viral entry and cell fusion. J. Virol. 62:2596–2604.
11. Campbell, M. E. M., J. W. Palfreyman, and C. M. Preston. 1984. Identification of herpes simplex virus DNA sequences which encode a trans-acting polypeptide responsible for stimulation of immediate early transcription. J. Mol. Biol. 180:1–19.
12. Claesson-Welsh, L., and P. G. Spear. 1986. Oligomerization of herpes simplex virus glycoprotein B. J. Virol. 60:803–806.
13. Coen, D. M., and P. A. Schaffer. 1980. Two distinct loci confer resistance to acycloguanosine in herpes simplex virus type 1. Proc. Natl. Acad. Sci. USA. 77:2265–2269.
14. Collins, P., B. A. Larder, N. M. Oliver, S. Kemp, I. W. Smith, and G. Darby. 1989. Characterization of a DNA polymerase mutant of herpes simplex virus from a severely immunocompromised patient receiving acyclovir. J. Gen. Virol. 70:375–382.
15. Corey, L., and P. Spear. 1986. Infections with herpes simplex viruses. N. Eng. J. Med. 314:686–691.
16. Corey, L., and P. Spear. 1986. Infections with herpes simplex viruses. N. Eng. J. Med. 314:749–757.
17. Crumpacker, C. S. 1989. Molecular targets of antiviral therapy. N. Engl. J. Med. 321:163–172.
18. Darby, G., H. J. Field, and S. A. Salisbury. 1981. Altered substrate specificity of herpes simplex virus thymidine kinase confers acyclovir-resistance. Nature. 289:81–83.
19. Davis-Poynter, N., S. Bell, T. Minson, and H. Browne. 1994. Analysis of the contributions of herpes simplex virus type 1 membrane proteins to the induction of cell-cell fusion. J. Virol. 68:7586–7590.
20. De Schryver, A., and A. Meheus. 1990. Epidemiology of sexually transmitted diseases: the global picture. Bull. World Health Organ. 68:639–654.
21. DeLuca, N. A., A. M. McCarthy, and P. A. Schaffer. 1985. Isolation and characterization of deletion mutants of herpes simplex virus type 1 in the gene encoding immediate early regulatory protein ICP4. J. Virol. 56:558–570.
22. Devlin, H., P. Geary, D. Pavan-Langston, Z. Dori, and E. C. Dunkel. 1993. Efficacy of CTC topical therapy during HSV-1-induced epithelial and stromal keratitis in the rabbit. Invest. Opthal. Vis. Sci. 34:1348.
23. Di Simone, C., and J. D. Baldeschwieier. 1992. Membrane fusion of mumps virus with ghost erythrocytes and CV-1 cells. Virology. 191:338–345.
24. Dixon, R. F., and P. A. Schaffer. 1980. Fine structure mapping and functional analysis of temperature-sensitive mutants in the gene encoding the herpes simplex virus type 1 immediate early protein VP175. J. Virol. 36:189–203.
25. Dunkel, E. C., P. A. Geary, J. Brooks, and D. Pavan-Langston. 1991. CTC 23 efficacy in vitro and on HSV-1-induced ocular epithelial and stromal disease in the rabbit. Antivir. Res. Supp. 1:135.
26. Dyer, A. P., B. W. Banfield, D. Martindale, D.-M. Spannier, and F. Tufaro. 1997. Dextran sulfate can act as an artificial receptor to mediate a type-specific herpes simplex virus infection via glycoprotein B. J. Virol. 71:191–198.
27. Elion, G. B., P. A. Furman, J. A. Fyfe, P. de Mirnada, L. Beauchamp, and H. J. Schaeffer. 1977. Selectively of action of an antiherpetic agent 9-(2-hydroxyethoxymethyl) guanine. Proc. Natl. Acad. Sci. USA. 74:5716–5720.
28. Ellis, M. N., P. M. Keller, J. A. Fyfe, J. L. Martin, J. F. Rooney, S. E. Straus, S. N. Lehrman, and D. W. Barry. 1987. Clinical isolate of herpes simplex virus type 2 that induces a thymidine kinase with altered substrate specificity. Antimicrob. Agents Chemother. 31:1117–1125.
29. Erice, A., C. Gil-Roda, J.-L. Perez, H. H. Balfour Jr., K. J. Sannerud, M. N. Hanson, G. Boivin, and S. Chou. 1997. Antiviral susceptibilites and analysis of UL97 and DNA polymerase sequences of clinical cytomegalovirus isolates from immunocompromised patients. J. Infect. Dis. 17S:1087–1092.
30. Erlich, K. S., L. Mills, P. Chatis, G. J. Mertz, D. F. Busch, S. E. Follansbee, R. M. Grant, and C. S. Crumpacker. 1989. Acyclovir-resistant herpes simplex virus infections in patients with the acquired immunodeficiency syndrome. N. Engl. J. Med. 320:293–296.
31. Frenkel, N., S. Silverstein, E. Cassai, and B. Roizman. 1973. RNA synthesis in cells productivity infected with herpes simplex virus. VIII. Control of transcription and of transcript abundancies of unique and common sequences of herpes simplex 1 and 2. J. Virol. 11:886–892.
32. Fyfe, J. A., P. M. Keller, P. A. Furman, R. L. Miller, and G. B. Elion. 1978. Thymidine kinase from herpes simplex virus phosphorylates the antiviral compound, 9-(2-hydroxyethoxymethyl) guanine. J. Biol. Chem. 253:8721–8727.
33. Gaudin, Y., C. Tuffereau, P. Durrer, J. Brunner, A. Flamand, and R. Ruigrok. 1999. Rabies virus-induced membrane fusion. Molec. Membr. Biol. 16:21–31.
34. Gerster, T., and R. G. Roeder. 1988. A herpesvirus trans-activating protein interacts with transcription factor OTF-1 and other cellular proteins. Proc. Natl. Acad. Sci. USA. 85:6347–6351.
35. Hall, L. M., K. G. Draper, R. J. Frink, R. H. Costa, and E. K. Wagner. 1982. Herpes simplex virus mRNA species mapping in EcoRI F fragment. J. Virol. 43:594–609.
36. Herold, B. C., R. J. Visalli, N. Susmarski, C. R. Brandt, and P. G. Spear. 1994. Glycoprotein C-independent binding of herpes simplex virus to cells requires cell surface heparan sulphate and glycoprotein B. J. Gen. Virol. 75:1211–1222.
37. Herold, B. C., D. WuDunn, N. Soltys, and P. G. Spear. 1991. Glycoprotein C of herpes simplex virus type 1 plays a principal role in the adsorption of virus to cells and in infectivity. J. Virol. 65:1090–1098.
38. Hoekstra, D., T. de Boer, K. Klappe, and J. Wilschut. 1984. Fluorescence method for measuring the kinetics of fusion between biological membranes. Biochemistry. 23:5675–5681.
39. Hoekstra, D., K. Klappe, T. de Boer, and J. Wilschut. 1985. Characterization of the fusogenic properties of Sendai virus: kinetics of fusion with erythrocyte membranes. Biochemistry. 24:4739–4745.
40. Holland, L. E., R. M. Sandri-Goldin, A. L. Goldin, J. C. Glorioso, and M. Levine. 1984. Transcriptional and genetic analyses of the herpes simplex virus type 1 genome: coordinates 0.29 to 0.45. J. Virol. 49:947–959.

41. Honess, R. W., and B. Roizman. 1974. Regulation of herpesvirus macromolecular synthesis. I. Cascade regulation of the synthesis of three groups of viral proteins. J. Virol. 14:8–19.
42. Honess, R. W., and B. Roizman. 1975. Regulation of herpesvirus macromolecular synthesis: Sequential transition of polypeptide synthesis requires functional viral polypeptides. Proc. Natl. Acad. Sci. USA. 72:1276–1280.
43. Hughson, F. M. 1997. Enveloped viruses: A common mode of membrane fusion? Curr. Biol. 7:R565–569.
44. Hwang, C. B. C., K. L. Ruffner, and D. M. Coen. 1992. A point mutation within a distinct conserved region of the herpes simplex virus DNA polymerase gene confers drug resistance. J. Virol. 66:1774–1776.
45. Hyndiuk, R. A., and D. B. Glasser. 1986. Herpes simplex keratitis., p. 343–368. In K. Tabbarra, and Hyndiuk, R. A. (ed.), Infections of the eye. Diagnosis and management. Little Brown, Boston.
46. Jones, K. A., and R. Tjian. 1985. SP1 binds to promoter sequences and activates herpes simplex virus immediate-early gene transcription in vitro. Nature. 317:179–182.
47. Keay, S., and B. Baldwin. 1991. Anti-idiotype antibodies that mimic gp86 of human cytomegalovirus inhibit viral fusion but not attachment. J. Virol. 65:5124–5128.
48. La Boissiere, S., T. Hughes, and P. O'Hare. 1999. HCF-dependent nuclear import of VP16. EMBO J. 18:480–489.
49. Lamb, R. A., S. B. Joshi, and R. E. Dutch. 1999. The paramyxovirus fusion protein forms an extremely stable core trimer: structural parallels to influenza virus haemagglutinin and HIV-1 gp41. Molec. Membr. Biol. 16:11–19.
50. Laquerre, S., R. Argnani, D. B. Anderson, S. Zucchini, R. Manservigi, and J. C. Glorioso. 1998. Heparan sulfate proteoglycan binding by herpes simplex virus type 1 glycoproteins B and C, which differ in their contributions to virus attachment, penetration, and cell-to-cell spread. J. Virol. 72:6119–6130.
51. Laughlin, C. A., R. J. Black, J. Feinberg, D. J. Freeman, J. Ramsey, M. A. Ussery, and R. J. Whitley. 1991. Resistance to antiviral drugs: although relatively new and poorly understood, viral resistace to drugs is an increasingly significant clinical issue. ASM News. 57:514–517.
52. Liesegang, T. J. 1989. Epidemiology of ocular herpes simplex. Natural history in Rochester, Minn., 1950 through 1982. Arch. Opthalmol. 107:1160–1165.
53. Liesegang, T. J., L. J. Melton, P. J. Daly, and D. M. Ilstrup. 1989. Epidemiology of ocular herpes simplex. Incidence in Rochester, Minn., 1950 through 1982. Arch. Opthalmol. 107:1155–1159.
54. Lium, E. K., C. A. Panagiotidis, X. Wen, and S. J. Silverstein. 1996. Repression of the aO gene by ICP4 during a productive herpes simplex virus infection. J. Virol. 70:3488–3496.
55. Lium, E. K., and S. J. Silverstein. 1997. Mutational analysis of the herpes simplex virus type 1 ICP0 C3HC4 zinc ring finger reveals a requirement for ICP0 in the expression of the essential a27 gene. J. Virol. 71:8602–8614.
56. Louie, A. Y., and T. J. Meade. 1998. A cobalt complex that selectively disrupts the structure and function of zinc fingers. Proc. Natl. Acad. Sci. USA. 95:6663–6668.
57. Loyter, A., V. Citovsky, and R. Blumenthal. 1988. The use of fluorescence dequenching measurement to follow viral membrane fusion. Methods Biochem. Anal. 33:129–164.
58. Mackem, S., and B. Roizman. 1982. Differentiation between a promoter and regulator regions of herpes simplex virus 1: The functional domains and sequence of a movable a regulator. Proc. Natl. Acad. Sci. USA. 79:4917–4921.
59. Mackem, S., and B. Roizman. 1982. Regulation of a genes of herpes simplex virus: The a27 promoter-thymidine kinase chimera is positively regulated in converted L cells. J. Virol. 43:1015–1023.
60. Mackem, S., and B. Roizman. 1982. Structural features of the herpes simplex virus alpha-gene 4, 0 and 27 promoter-regulatory sequences which confer alpha-regulation on chimeric thymidine kinase genes. J. Virol. 44:939–946.
61. McMahan, L., and P. A. Schaffer. 1990. Repressing and enhancing functions of the herpes simplex virus regulatory protein ICP27 map to C-terminal regions and are required to modulate viral gene expression very early in infection. J. Virol. 64:3471–3485.
62. Miller, N., and L. M. Hutt-Fletcher. 1988. A monoclonal antibody to glycoprotein gp85 inhibits fusion but not attachment of Epstein-Barr virus. J. Virol. 62:2366–2372.
63. Montgomery, R. I., M. S. Warner, B. J. Lum, and P. G. Spear. 1996. Herpes simplex virus-1 entry into cells mediated by a novel member of the TNF/NGF receptor family. Cell. 87:427–436.
64. Navarro, D., P. Paz, and L. Pereira. 1992. Domains of herpes simplex virus 1 glycoprotein B that function in virus penetration, cell-to-cell spread, and cell fusion. Virology. 186:99–112.
65. Novotny, M. J., M. L. Parish, and P. G. Spear. 1996. Variability of herpes simplex virus gL and anti-gL antibodies that inhibit cell fusion but not viral infectivity. Virology. 221:1–13.
66. Nugier, F., J. N. Colin, M. Aymard, and M. Langlois. 1992. Occurence and characterization of acyclovir-resistance herpes simplex virus isolates: report on a two-year sensitivity screening survey. J. Med. Virol. 36:1–12.
67. O'Hare, P., C. R. Goding, and A. Haigh. 1988. Direct combinatorial interaction between a herpes simplex virus regulatory protein and a cellular octamer-binding factor mediates specific induction of virus immediate-early gene expression. EMBO J. 7:4231–4238.
68. Ostrow, R. S., S. Coughlin, R. C. McGlennen, Z. Liu, D. Zelterman, and A. J. Faras. 1994. Topical CTC-96 accelerates wart growth in rabbits infected with cottontail rabbit papillomavirus. Antivir. Res. 24:27–35.
69. Pinol-Roma, S., S. A. Adam, Y. Do Choi, and G. Dreyfuss. 1989. Ultraviolet-induced cross-linking of RNA to proteins in vivo. Methods Enzym. 180:410–418.
70. Pope, L. E., J. F. Marcelletti, L. R. Katz, J. Y. Lin, D. H. Katz, M. L. Parish, and P. G. Spear. 1998. The anti-herpes simplex virus activity of n-docosanol includes inhibition of the viral entry process. Antivir. Res. 40:85–94.
71. Post, L. E., S. Mackem, and B. Roizman. 1981. Regulation of alpha genes of HSV: expression of chimeric genes produced by fusion of thymidine kinase with alpha gene promoters. Cell. 24:555–565.
72. Preston, C. M. 1979. Control of herpes simplex virus type 1 mRNA synthesis in cells infected with wild-type virus or the temperature-sensitive mutant tsK. J. Virol. 29:275–284.
73. Rajcani, J., and A. Vojvodova. 1998. The role of herpes simplex virus glycoproteins in the virus replication cycle. Acta Virol. 42:103–118.
74. Reusser, P. 1998. Current concepts and challenges in the prevention and treatment of viral infections in immunocompromised cancer patients. Support Care Cancer. 6:39–45.

75. Rice, S. A., and D. M. Knipe. 1988. Gene-specific trans-activation by the herpes simplex virus type 1 alpha protein ICP27. J. Virol. 62:3814–3823.
76. Roizman, B. 1968. An inquiry into the mechanisms of recurrent herpes infections in man., p. 283. In M. Pollard (ed.), Perspectives in virology., vol. 4. Harper & Row, New York.
77. Schnipper, L. E., and C. S. Crumpacker. 1980. Resistance of herpes simplex virus to acycloguanosine: role of thymidine kinase and DNA polymerase loci. Proc. Natl. Acad. Sci. USA. 77:2270–2273.
78. Shieh, M.-T., D. WuDunn, R. I. Montgomery, J. D. Esko, and P. G. Spear. 1992. Cell surface receptors for herpes simplex virus are heparan sulfate proteoglycans. J. Cell Biol. 116:1273–1281.
79. Showalter, S. D., M. Zweig, and B. Hampar. 1981. Monoclonal antibodies to herpes simplex virus type 1 proteins, including the immediate-early protein ICP4. Infec. Immun. 34:684–692.
80. Sinangil, F., A. Loyter, and D. J. Volsky. 1988. Quantitative measurement of human immunodeficiency virus and cultured cells using membrane fluorescence dequenching. FEBS Lett. 239:88–92.
81. Sodeik, B., M. W. Ebersold, and A. Helenius. 1997. Microtubule-mediated transport of incoming herpes simplex virus 1 capsids to the nucleus. J. Cell Biol. 136:1007–1021.
82. Spear, P. G. 1993. Entry of alphaherpesviruses into cells. Sem. Virol. 4:167–180.
83. Spear, P. G. 1985. Glycoproteins specified by herpes simplex virus., p. 315–356. In B. Roizman (ed.), The Herpesviruses., vol. 3. Plenum Press, New York.
84. Stewart, J. A., S. E. Reff, P. E. Pellet, L. Corey, and R. J. Whitely. 1995. Herpesvirus infection in persons infected with human immunodeficiency virus. Clin. Infec. Dis. 21 Supp. 1:S114–120.
85. Swanstrom, R. I., K. Pivo, and E. K. Wagner. 1974. Restricted transcription of the herpes simplex virus genome occurring early after infection and in the presence of metabolic inhibitors. Virology. 66:140–150.
86. Terry-Allison, T., R. Montgomery, J. C. Whitbeck, R. Xu, G. H. Cohen, R. J. Eisenberg, and P. G. Spear. 1998. HveA (herpesvirus entry mediator A), a coreceptor for herpes simplex virus entry, also participates in virus-induced cell fusion. J. Virol. 72:5802–5810.
87. Thomas, J., and B. T. Rouse. 1997. Immunopathogenesis of herpetic ocular disease. Immunol. Res. 16:375–386.
88. Vogt, P. E., C. B. Hartline, T. P. Gerchow, and E. R. Kern. 1992. Antiviral activity of a series of cobalt containing complexes against herpesvirus infection in vitro and in vivo. Antivir. Res. 17S:114.
89. Watson, R. J., and J. B. Clements. 1978. Characterization of transcription-deficient temperature-sensitive mutants of herpes simplex virus. Virology. 91:364–379.
90. Weissenhorn, W., A. Dessen, L. J. Calder, S. C. Harrison, J. J. Skehel, and D. C. Wiley. 1999. Structural basis for membrane fusion by enveloped viruses. Molec. Membr. Biol. 16:3–9.
91. Whitley, R. J. 1990. Herpes simplex viruses., p. 1843–1887. In B. N. Fields, and Knipe, D.M. (ed.), Virology, 2 ed. Raven Press, Ltd., New York.
92. Wood, M. J. 1996. Antivirals in the context of HIV disease. J. Antimicrob. Chemother. 37 Supp. B:97–112.
93. Wooley, P. H., and J. D. Whalen. 1992. The influence of superoxide scavenging compound CTC 23 on type II collagen-induce arthritis in mice. Agents Actions. 35:273–279.
94. WuDunn, D., and P. G. Spear. 1989. Initial interaction of herpes simplex virus with cells is binding to heparan sulfate. J. Virol. 63:52–58.
95. Zhou, Z. H., D. H. Chen, J. Jakana, F. J. Rixon, and W. Chiu. 1999. Visualization of tegument-capsid interactions and DNA in intact herpes simplex virus type 1 virions. J. Virol. 73:3210–3218.
96. Zhu, Q., and R. J. Courtney. 1988. Chemical crosslinking of glycoproteins on the envelope of herpes simplex virus. Virology. 167:377–384.

What is claimed is:

1. A method of prophylaxis against the infection of a cell by a non-enveloped virus or an influenza virus comprising contacting the cell with a compound having the structure:

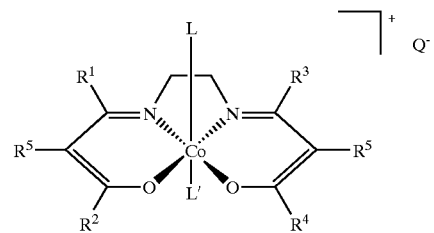

wherein each of $R^1$, $R^2$, $R^3$, and $R^4$ is the same or different and is an alkyl group, a phenyl group or a substituted derivative of a phenyl group;

wherein $R^5$ is hydrogen, a halide, an alkoxide group, an alkyl group or OH;

wherein each of L and L' is the same or different and is $NH_3$, 2-methylimidazole, an imidazole, or a substituted derivative of an imidazole; and wherein $Q^-$ is a soluble, pharmaceutically acceptable negative ion, so as to thereby provide prophylaxis against infection of the cell by the non-enveloped virus or an influenza virus.

2. The method of claim 1, wherein each of $R^1$, $R^2$, $R^3$, and $R^4$ is $CH_3$; $R^5$ is H or Cl; L=L'=imidazole or 2-methylimidazole; and $Q^-$ is $Cl^-$ or $Br^-$.

3. The method of claim 1, wherein the compound has the structure:

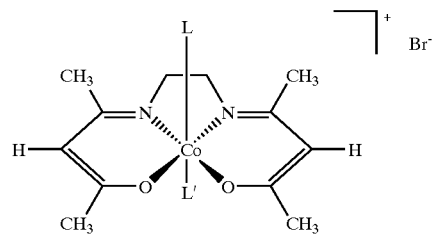

wherein L=L'=2-methylimidazole.

4. The method of claim 1, wherein the virus is a non-enveloped virus.

5. The method of claim 1, wherein the virus is an influenza virus.

6. The method of claim 4, wherein the non-enveloped virus is poliovirus or adenovirus.

7. The method of claim 6, wherein the non-enveloped virus is adenovirus.

8. A method of treating a subject infected with a non-enveloped virus or an influenza virus comprising administering to the subject an antiviral composition comprising an antiviral effective amount of a compound having the structure:

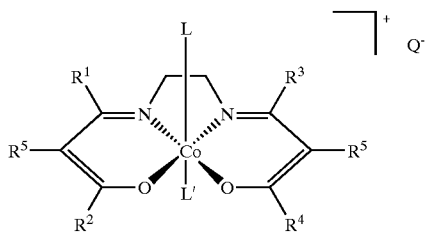

wherein each of $R^1$, $R^2$, $R^3$, and $R^4$ is the same or different and is an alkyl group, a phenyl group or a substituted derivative of a phenyl group;
wherein $R^5$ is hydrogen, a halide, an alkoxide group, an alkyl group or OH;
wherein each of L and L' is the same or different and is $NH_3$, 2-methylimidazole, an imidazole, or a substituted derivative of an imidazole; and
wherein $Q^-$ is a soluble, pharmaceutically acceptable negative ion,
so as to thereby treat the subject infected by the non-enveloped virus or influenza virus.

9. A method of prophylaxis against infection of a subject by a non-enveloped virus or an influenza virus comprising administering to the subject an antiviral composition comprising an antiviral effective amount of a compound having the structure:

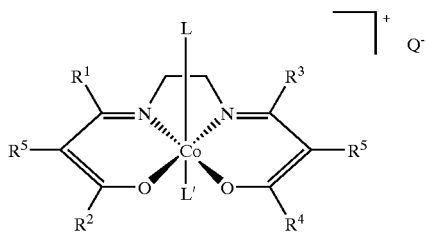

wherein each of $R^1$, $R^2$, $R^3$, and $R^4$ is the same of different and is an alkyl group, a phenyl group or a substituted derivative of a phenyl group;
wherein $R^5$ is hydrogen, a halide, an alkoxide group, an alkyl group or OH;
wherein each of L and L' is the same or different and is $NH_3$, 2-methylimidazole, an imidazole, or a substituted derivative of an imidazole; and
wherein $Q^-$ is a soluble, pharmaceutically acceptable negative ion,
so as to thereby provide prophylaxis against infection of the subject by the non-enveloped virus or influenza virus.

10. The method of claim 9, wherein the route of administration is oral, intramuscular injection, intraperitoneal injection, aerosol, or intravenous infusion.

11. The method of claim 8, wherein the compound has the structure:

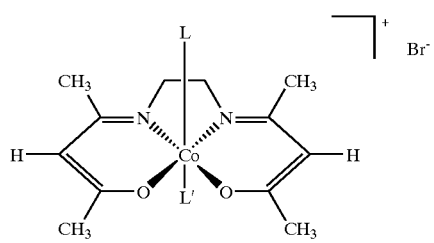

wherein L=L'=2-methylimidazole.

12. The method of claim 8, wherein the virus is a non-enveloped virus.

13. The method of claim 8, wherein the virus is an influenza virus.

14. The method of claim 13, wherein the non-enveloped virus is poliovirus or adenovirus.

15. The method of claim 14, wherein the non-enveloped virus is adenovirus.

16. The method of claim 9, wherein the compound has the structure:

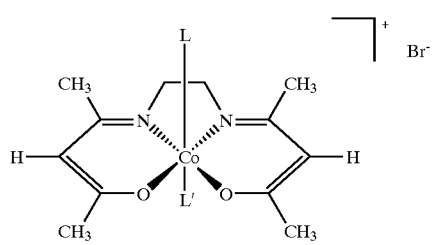

wherein L=L'=2-methylimidazole.

17. The method of claim 9, wherein the virus is a non-enveloped virus.

18. The method of claim 9, wherein the virus is an influenza virus.

19. The method of claim 18, wherein the non-enveloped virus is poliovirus or adenovirus.

20. The method of claim 19, wherein the non-enveloped virus is adenovirus.

21. The method of claim 6, wherein the non-enveloped virus is polio virus.

22. The method of claim 14, wherein the non-enveloped virus is polio virus.

23. The method of claim 19, wherein the non-enveloped virus is polio virus.

* * * * *